United States Patent
Nakao et al.

(10) Patent No.: US 10,933,044 B2
(45) Date of Patent: Mar. 2, 2021

(54) MARINE ORGANISM-DERIVED EXTRACT, COMPOUND, AND MEDICAL COMPOSITION HAVING NICHE FORMATION SUPPRESSING ACTIVITY OF LEUKEMIC STEM CELLS

(71) Applicants: WASEDA UNIVERSITY, Shinjuku-ku (JP); KABUSHIKI KAISHA YAKULT HONSHA, Minato-ku (JP)

(72) Inventors: Yoichi Nakao, Shinjuku-ku (JP); Shigetaka Asano, Shinjuku-ku (JP); Daisuke Arai, Shinjuku-ku (JP); Yukari Kase, Shinjuku-ku (JP); Teppei Shimomoto, Shinjuku-ku (JP)

(73) Assignees: WASEDA UNIVERSITY, Shinjuku-ku (JP); KABUSHIKI KAISHA YAKULT HONSHA, Minato-ku (JP)

( * ) Notice: Subject to any disclaimer, the term of this patent is extended or adjusted under 35 U.S.C. 154(b) by 0 days.

(21) Appl. No.: 16/069,647

(22) PCT Filed: Jan. 12, 2017

(86) PCT No.: PCT/JP2017/000856
§ 371 (c)(1),
(2) Date: Jul. 12, 2018

(87) PCT Pub. No.: WO2017/122736
PCT Pub. Date: Jul. 20, 2017

(65) Prior Publication Data
US 2019/0022045 A1 Jan. 24, 2019

(30) Foreign Application Priority Data
Jan. 13, 2016 (JP) .............................. JP2016-004523

(51) Int. Cl.
| | |
|---|---|
| *A61K 31/215* | (2006.01) |
| *A61K 35/655* | (2015.01) |
| *A61K 45/00* | (2006.01) |
| *C07C 69/74* | (2006.01) |
| *A61P 35/02* | (2006.01) |
| *A61K 45/06* | (2006.01) |

(52) U.S. Cl.
CPC .......... *A61K 31/215* (2013.01); *A61K 35/655* (2015.01); *A61K 45/00* (2013.01); *A61K 45/06* (2013.01); *A61P 35/02* (2018.01); *C07C 69/74* (2013.01); *C07C 2603/16* (2017.05)

(58) Field of Classification Search
None
See application file for complete search history.

(56) References Cited

U.S. PATENT DOCUMENTS

| | | |
|---|---|---|
| 2012/0121535 A1 | 5/2012 | Ishikawa et al. |
| 2012/0244116 A1 | 9/2012 | Hiwase et al. |
| 2015/0093355 A1 | 4/2015 | Hiwase et al. |
| 2016/0304616 A1 | 10/2016 | Hiwase et al. |

FOREIGN PATENT DOCUMENTS

| | | |
|---|---|---|
| CN | 101113134 | 1/2008 |
| CN | 103288790 | 9/2013 |
| JP | 2013-505968 A | 2/2013 |
| WO | WO 2010/101257 A1 | 9/2010 |
| WO | WO 2011/038467 A1 | 4/2011 |
| WO | WO 2013/009690 A2 | 1/2013 |
| WO | WO 2013/070807 A1 | 5/2013 |

OTHER PUBLICATIONS

International Search Report dated Apr. 18, 2017, in PCT/JP2017/000856, filed Jan. 12, 2017.
Tsuda, M. et al.,"Stelliferins A-F, New Antineoplastic Isomalabaricane Triterpenes from the Okinawan Marine Sponge *Jaspis Stellifera*," Tetrahedron, vol. 47, No. 12/13, pp. 2181-2194.
Oku, N. et al., "New Isomalabaricane Triterpenes from the Marine Sponge *Stelletta globostellata* That Induce Morphological Changes in Rat Fibroblasts", Journal of Natural Products, vol. 63, No. 2, 2000, pp. 205-209.
Hartwell, K. et al., "Niche-based screening identifies small-molecule inhibitors of leukemia stem cells", Nature Chemical Biology, vol. 9, Dec. 2013, pp. 840-851.
Office Action as received in the corresponding Chinese Patent Application No. 201780006491.2 dated Dec. 15, 2020 w/English Translation, 14 pages.

*Primary Examiner* — Ana Z Muresan
(74) *Attorney, Agent, or Firm* — Oblon, McClelland, Maier & Neustadt, L.L.P.

(57) ABSTRACT

Using the cobblestone area (CA) formation inhibitory activity of human leukemic stem cell-like cells as an indicator, a fraction having the activity has been extracted from the fat-soluble fraction of Porifera, then, a compound having the activity has been isolated and purified from the aforementioned fraction, and then, the structure thereof has been determined, so that a Stelliferin compound comprising a novel compound has been identified. Moreover, it has been found that the isolated and purified Stelliferin compound significantly suppresses the niche formation of leukemic stem cell-like cells derived from human chronic myelogenous leukemia (CML) having resistance to existing antitumor agents and enhances the effects of antitumor agents on the cells. The present invention provides a pharmaceutical composition having inhibitory or suppressive activity against the niche formation of leukemic stem cells, a prophylactic agent against the recurrence of malignant tumor, which involves the combined use of other antitumor drugs, and the like.

7 Claims, 27 Drawing Sheets

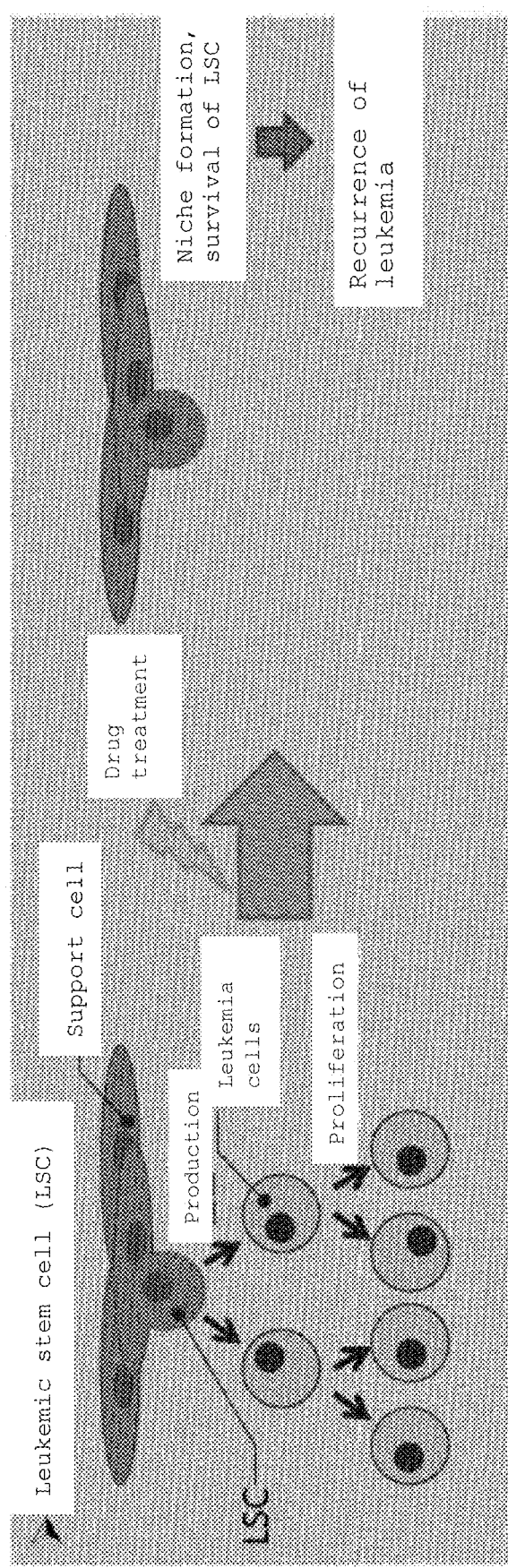
[Figure 1A]

[Figure 1B]
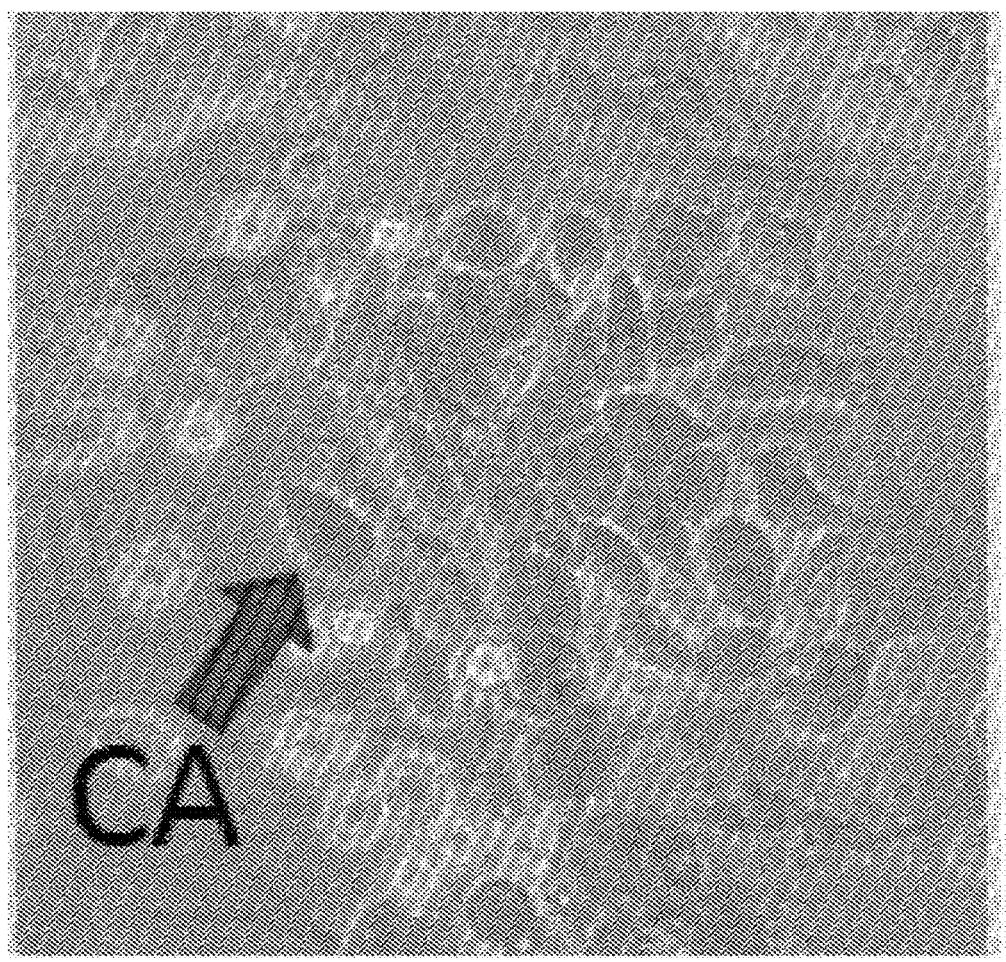

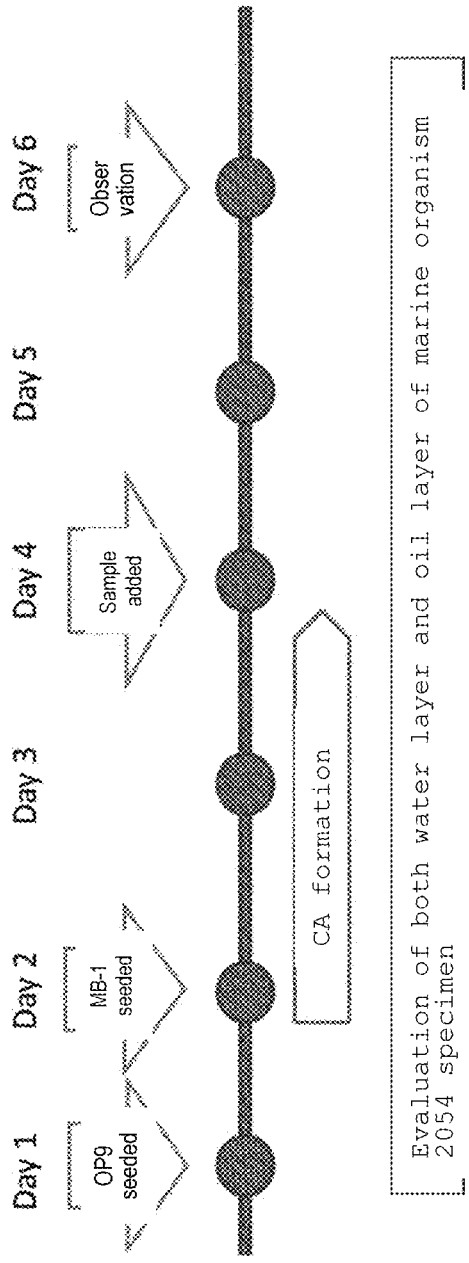
[Figure 2A]
Screening method
- Using 96-well plate
- Day 1: Seeding OP9 (9.0 × 10³ cells/well)
- Day 2: Seeding MB-i (GFP) (2.5 × 10³ cells/well)
- Day 4: Adding sample (2 μL), diluted 5 times to prepare 4 solutions differ in concentration (10 μg/mL, 2 μg/mL, 0.4 μg/mL, 0.08 μg/mL)
- Day 6: Fixed with 4% paraformaldehyde, nuclear-stained with hoechst 33342, photographed

[Figure 2B]
Screening method
Evaluation
[Criteria]
①Inhibition of CA formation
②Sample having no significant effect on OP9 cells
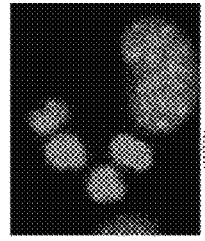
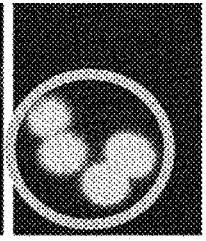
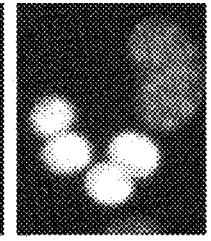
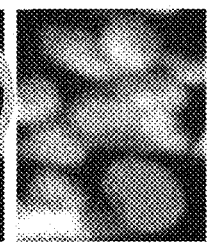
cobblestone area (CA)
During CA formation / During non-CA formation
Purple: hoechst33342
Green: GFP
merge
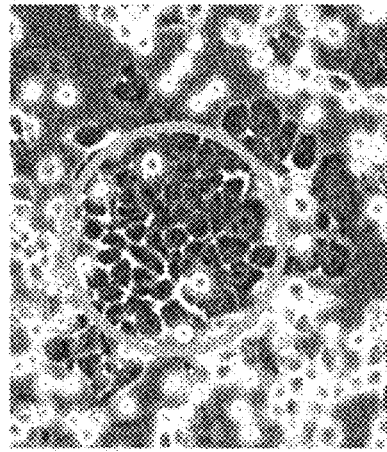
CA formation by MB-1 and OP9 (bright field)

[Figure 3]
Fractionation of S12111 with solvent
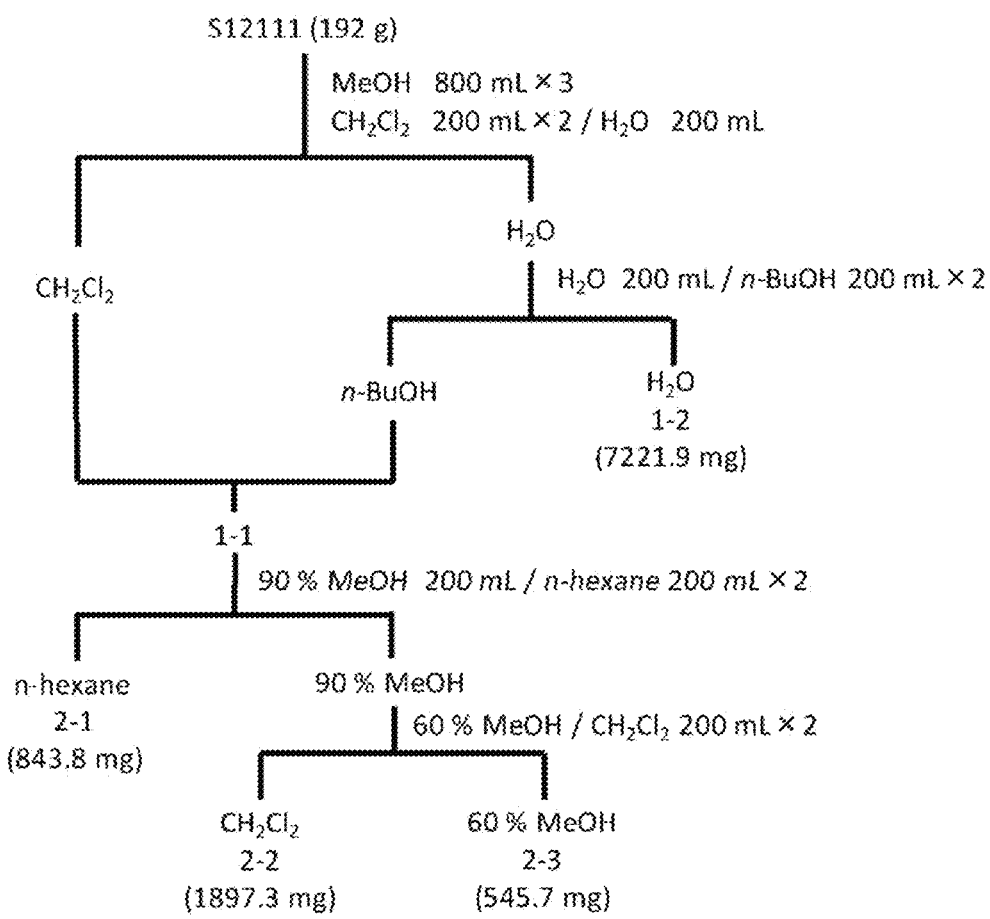

[Figure 4]
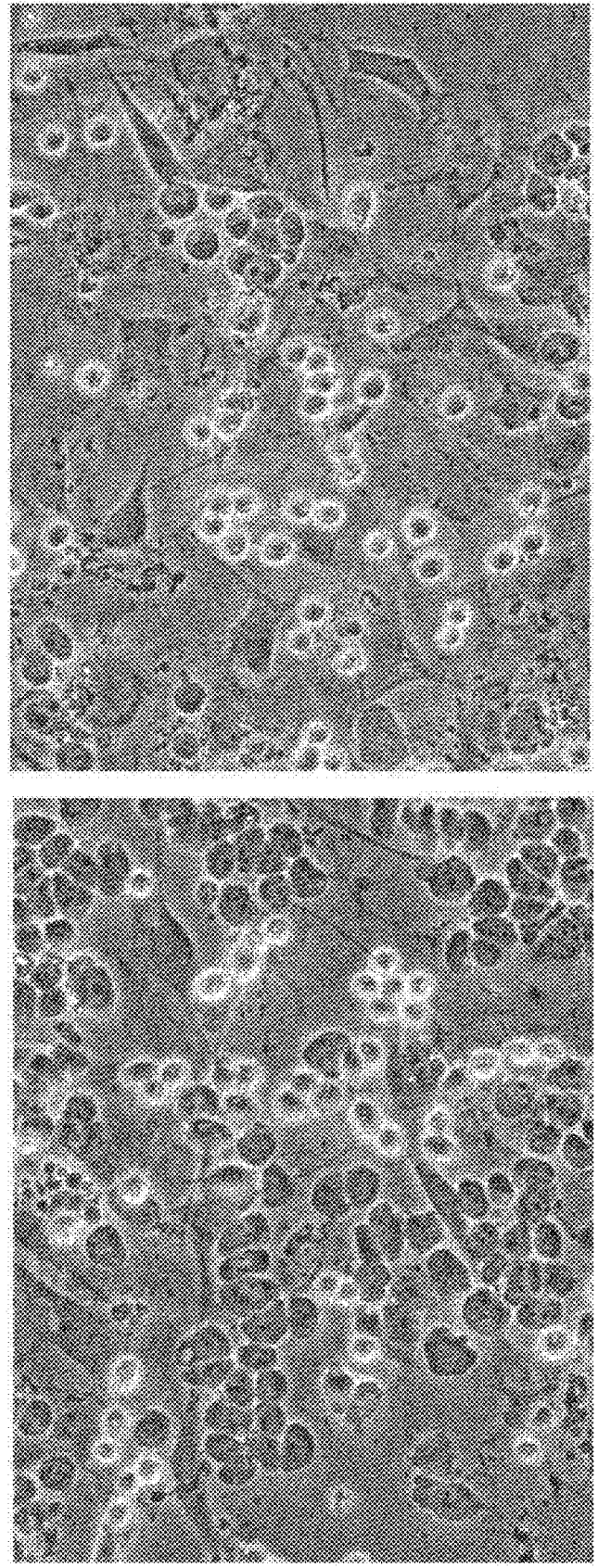

[Figure 5]
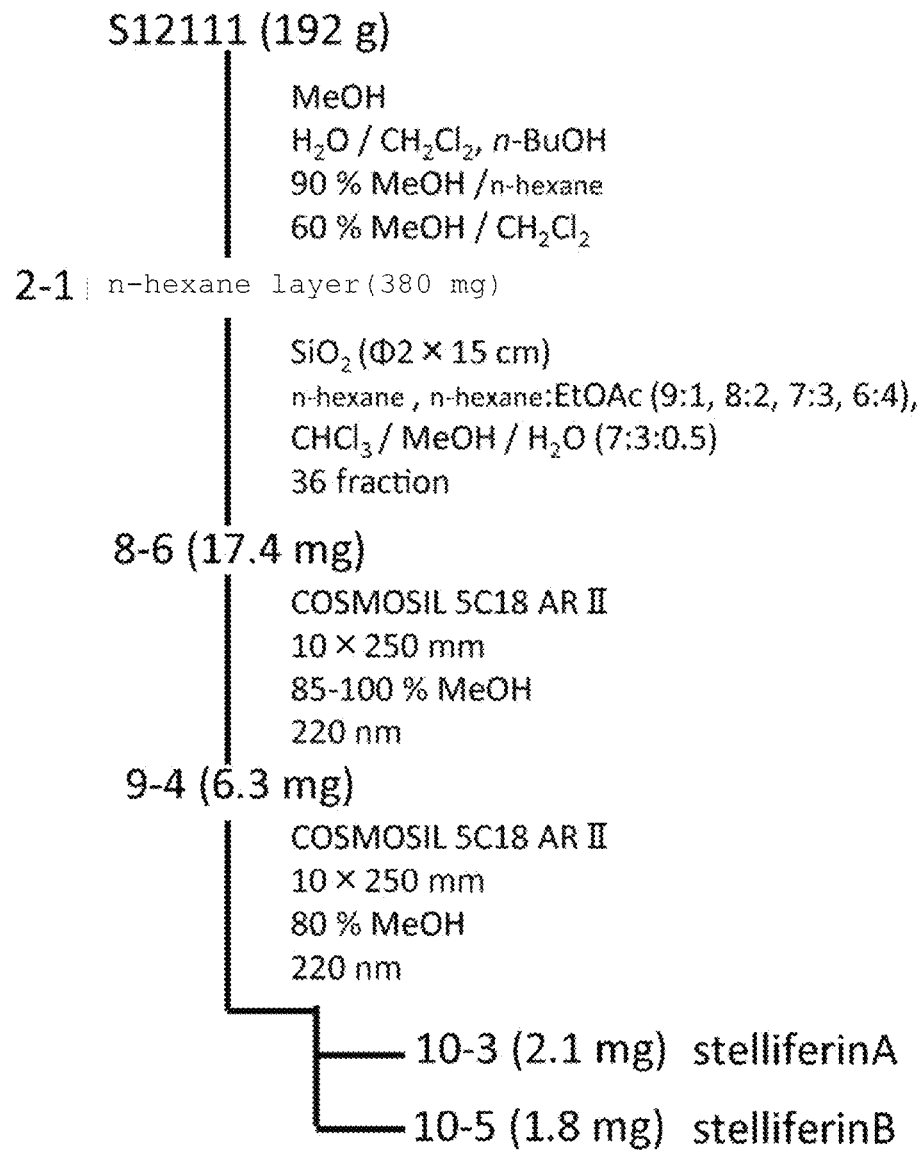

[Figure 6]
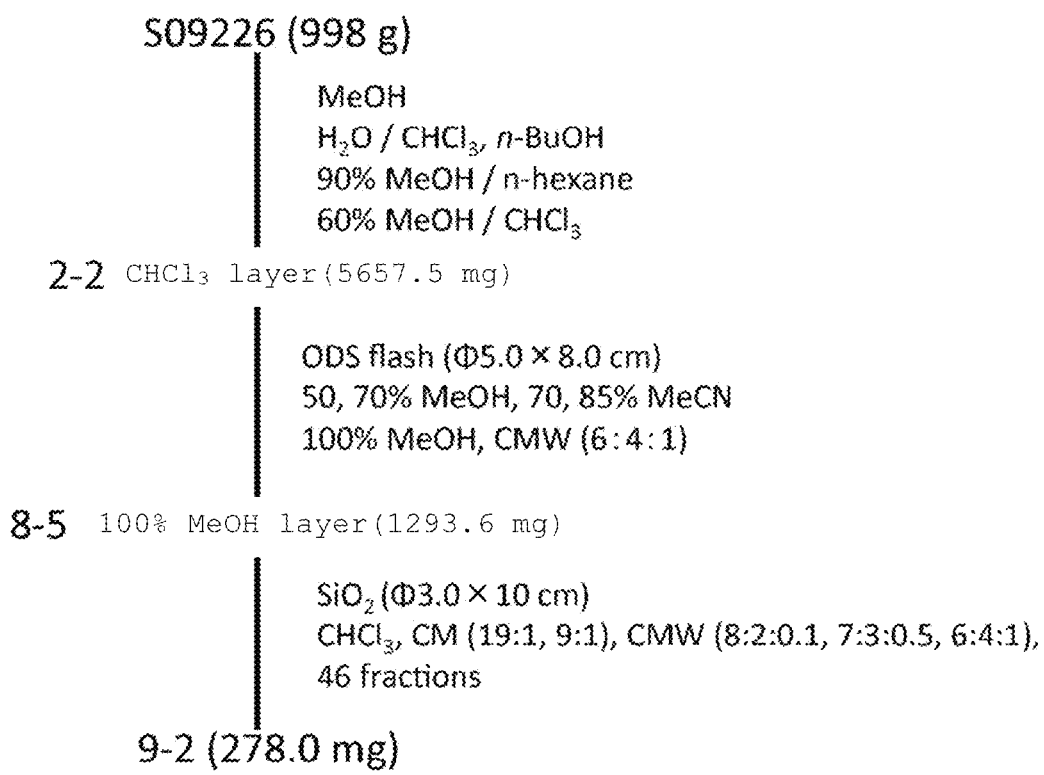

[Figure 7A]
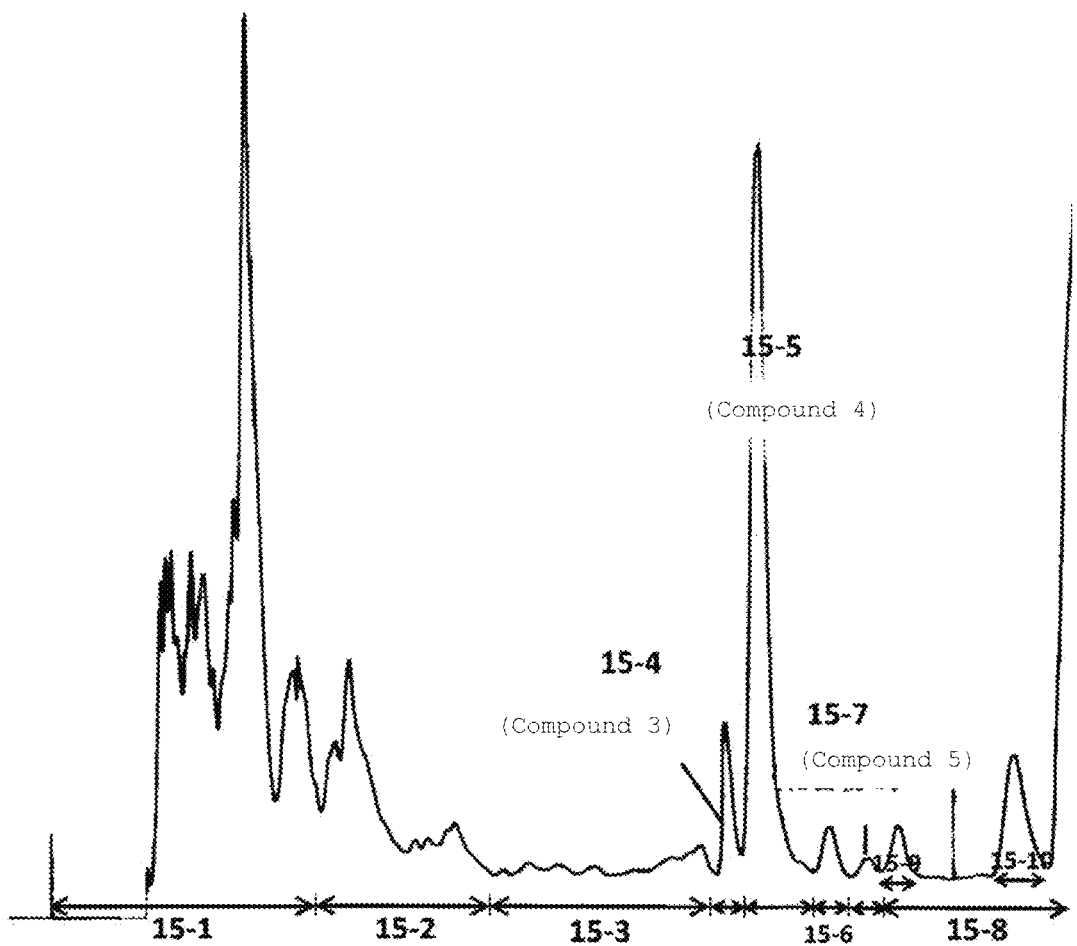

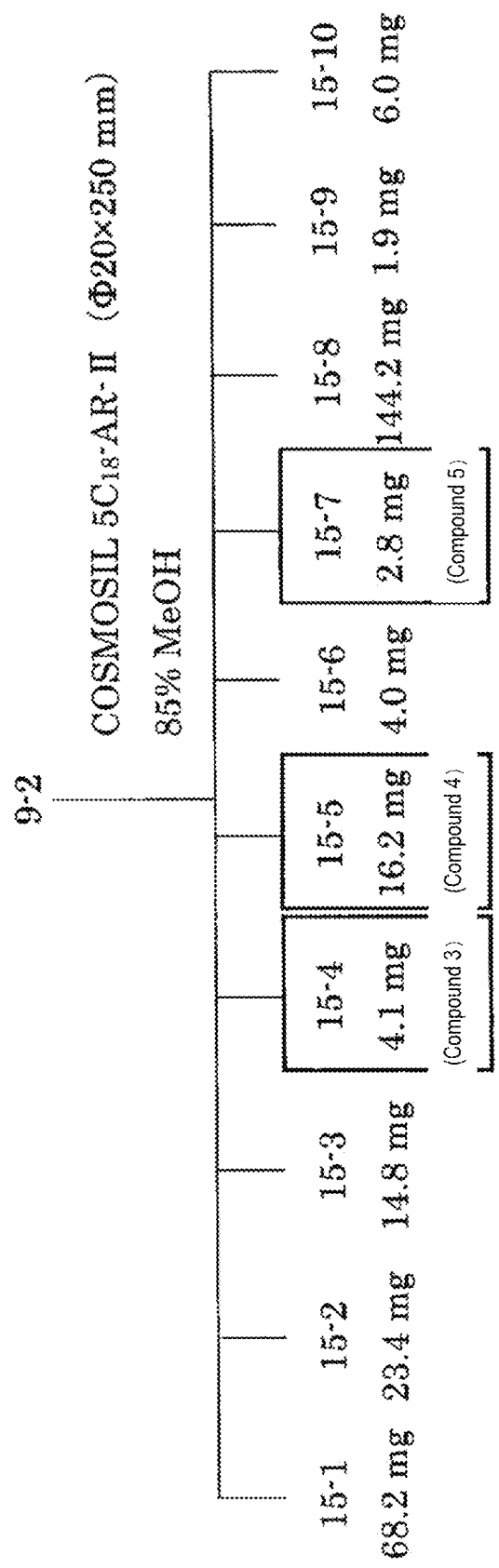
[Figure 7B]

[Figure 8]
S12111 10-3 (stelliferin A)
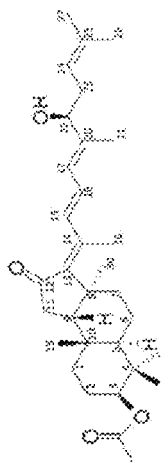
stelliferin A
($C_{32}H_{48}O_4$, 496.3553)
| atom | $\delta^{13}C$ CDCl$_3$ | $^1H$ CDCl$_3$ | COSY | HMBC ($^{13}C \to ^1H$) |
|---|---|---|---|---|
| 1 | 33.23 | 1.35 m, 1.58 m | | H-19 |
| 2 | 25.35 | 1.82 m | H-3 | |
| 3 | 80.98 | 4.53 dd | H-2 | H-28, H-29 |
| 4 | 38.47 | | | H-5, H-28, H-29 |
| 5 | 46.79 | 1.75 m | H-7 | H-19, H-28, H-29 |
| 6 | 18.48 | 1.44 m | | |
| 7 | 38.36 | 2.06 m | H-6 | H-30 |
| 8 | 44.77 | | | H-11, H-30 |
| 9 | 50.43 | 1.74 m | | H-19, H-30 |
| 10 | 35.65 | | | H-5, H-19 |
| 11 | 36.98 | 2.17 m | | H-11 |
| 12 | 206.68 | | | H-18, H-30 |
| 13 | 146.24 | | | H-18 |
| 14 | 142.66 | | | H-18 |
| 15 | 132.37 | 7.95 d | H-16 | H-15, H-23, H-22 |
| 16 | 130.42 | 6.83 dd | H-15, H-17 | H-15 |
| 17 | 126.46 | 6.22 d | H-16 | H-5 |
| 18 | 16.18 | 1.98 s | | H-21 |
| 19 | 22.56 | 0.96 s | | |
| 20 | 143.40 | | | H-17, H-21 |
| 21 | 12.97 | 1.80 s | | |
| 22 | 76.61 | 4.08 t | H-23 | H-26, H-27 |
| 23 | 34.51 | 2.26 m | H-22, H-24 | H-26, H-27 |
| 24 | 119.88 | 5.10 t | H-23 | H-27 |
| 25 | 136.04 | | | H-26 |
| 26 | 18.21 | 1.61 s | | H-29 |
| 27 | 26.10 | 1.69 s | | H-5,H-29 |
| 28 | 29.20 | 0.88 s | | |
| 29 | 17.15 | 0.86 s | | |
| 30 | 24.92 | 1.33 s | | |
| 3-CH$_3$CO | 21.45 | 2.03 s | | H-3, 3-CH$_3$CO |
| 3-CH$_3$CO | 171.20 | | | |

[Figure 9]
S12111 10-5 (stelliferin B)
| Atom | δ13C CDCl3 | 1H CDCl3 | COSY | HMBC (13C→1H) |
|---|---|---|---|---|
| 1 | 33.24 | 1.34 m | | H-19 |
| 2 | 25.34 | | | |
| 3 | 81.01 | 4.55 dd | | H-28, H-29 |
| 4 | 38.37 | | | H-28, H-29 |
| 5 | 46.90 | 1.75 m | | H-19, H-28, H-29 |
| 6 | 18.58 | | | |
| 7 | 39.65 | | | H-30 |
| 8 | 44.81 | | | H-11, H-30 |
| 9 | 50.36 | | | H-19, H-30 |
| 10 | 35.66 | | | H-19 |
| 11 | 36.86 | 2.14 dd | | H-11, H-18 |
| 12 | 207.76 | | | H-18, H-30 |
| 13 | 146.60 | | | H-18 |
| 14 | 141.77 | | | H-18 |
| 15 | 132.37 | 6.52 d | H-16 | |
| 16 | 131.83 | 6.85 dd | H-15, H-17 | |
| 17 | 125.37 | 6.25 d | H-16 | |
| 18 | 14.71 | 2.28 s | | H-21 |
| 19 | 22.53 | 0.98 s | | |
| 20 | 144.23 | | | H-21 |
| 21 | 13.77 | 1.83 s | | H-21 |
| 22 | 76.91 | 4.08 t | H-23 | |
| 23 | 34.73 | 2.26 br | H-22, H-24 | |
| 24 | 119.79 | 5.10 t | H-23 | H-26, H-27 |
| 25 | 136.04 | | | H-26, H-27 |
| 26 | 18.25 | 1.62 s | | H-27 |
| 27 | 26.14 | 1.71 s | | H-26 |
| 28 | 29.20 | 0.88 s | | H-29 |
| 29 | 17.16 | 0.85 s | | H-28 |
| 30 | 25.99 | 1.35 s | | |
| 3-CH3CO | 21.45 | 2.03 s | | |
| 3-CH3CO | 171.21 | | | 3-CH3CO |
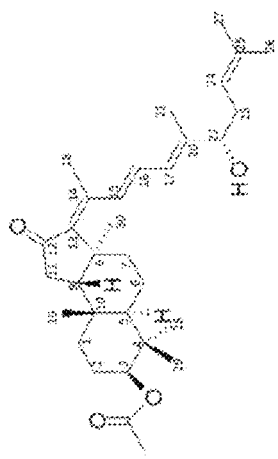
stelliferin B
($C_{32}H_{48}O_4$, 496.3553)

[Figure 10A]
S0926 15-4
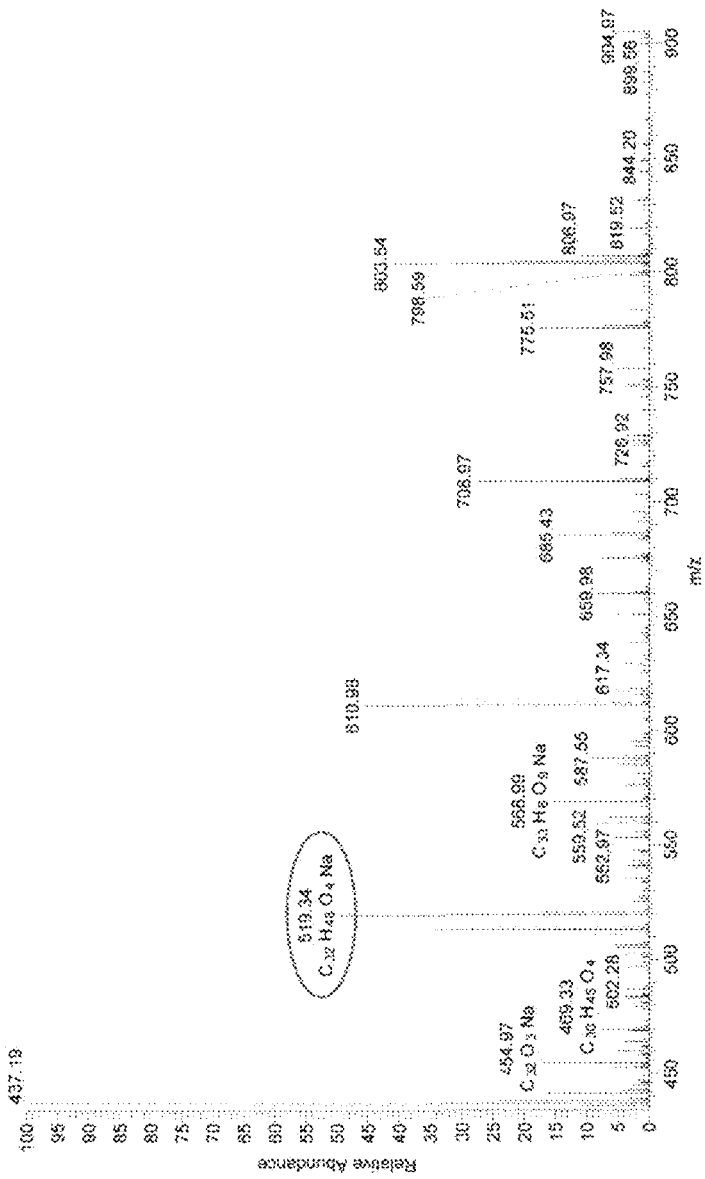

[Figure 10B]
S09226 15-4
| Atom | δ¹³C CDCl₃ | ¹H CDCl₃ | COSY | HMBC (¹³C→¹H) |
|---|---|---|---|---|
| 1 | 29.62 | 1.17 m | | H-19 |
| 2 | 24.54 | 1.67 br | H-3 | |
| 3 | 78.20 | 4.68 t | H-2 | |
| 4 | 37.55 | | | H-28, H-29 |
| 5 | 41.74 | 2.20 m | | H-5, H-28, H-29 |
| 6 | 18.31 | | | H-19, H-28, H-29 |
| 7 | 38.77 | 2.01 m | | H-5 |
| 8 | 44.86 | | | H-30 |
| 9 | 50.66 | 1.75 m | | H-11, H-30 |
| 10 | 35.71 | | | H-11, H-19, H-30 |
| 11 | 36.92 | 2.11 m | | H-5, H-19 |
| 12 | 206.99 | | | |
| 13 | 145.44 | | | H-11 |
| 14 | 142.59 | | | H-15, H-18, H-30 |
| 15 | 132.44 | 7.95 d | | H-16, B-18 |
| 16 | 130.35 | 6.73 dd | H-16 | H-17, H-18 |
| 17 | 126.49 | 6.20 d | H-15, H-17 | H-15, H-16, H-21, H-22 |
| 18 | 16.21 | 1.96 s | H-16 | H-15 |
| 19 | 22.55 | 0.94 s | | |
| 20 | 143.29 | | | H-21 |
| 21 | 12.97 | 1.75 s | | H-17, H-22 |
| 22 | 77 | 4.03 t | H-23 | H-17, H-21 |
| 23 | 34.51 | 2.25 m | H-22, H-24 | H-22, H-23, H-26, H-27 |
| 24 | 119.84 | 5.03 t | H-23 | H-23, H-26, H-27 |
| 25 | 135.44 | | | H-27 |
| 26 | 18.22 | 1.57 s | | H-26 |
| 27 | 26.11 | 1.65 s | | H-29 |
| 28 | 27.97 | 0.81 s | | H-5, H-28 |
| 29 | 21.57 | 0.85 s | | |
| 30 | 24.38 | 1.33 s | | |
| 3-CH₃CO | 21.47 | 1.96 s | | 3-CH₃CO |
| 3-CH₃CO | 170.66 | | | |
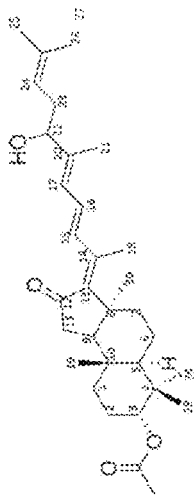
S09226.15-4
($C_{32}H_{48}O_4$, 496.3553)

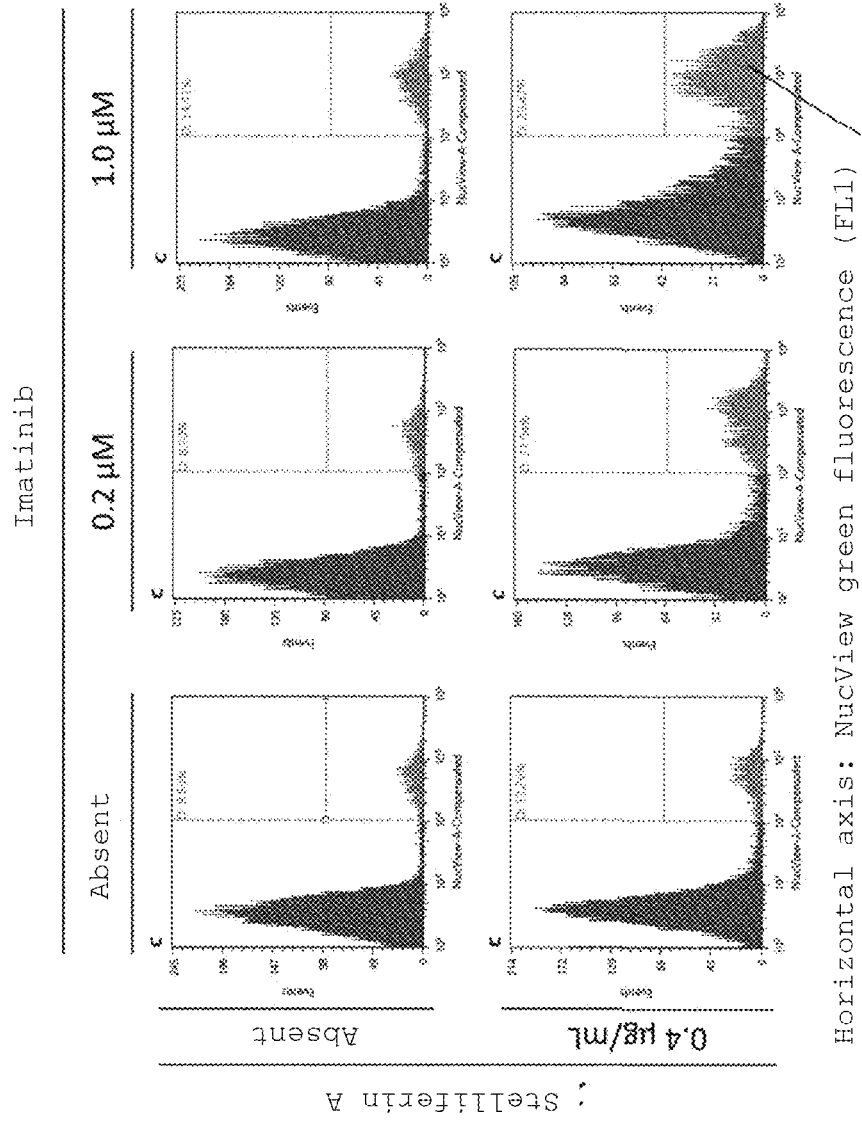
[Figure 11A]

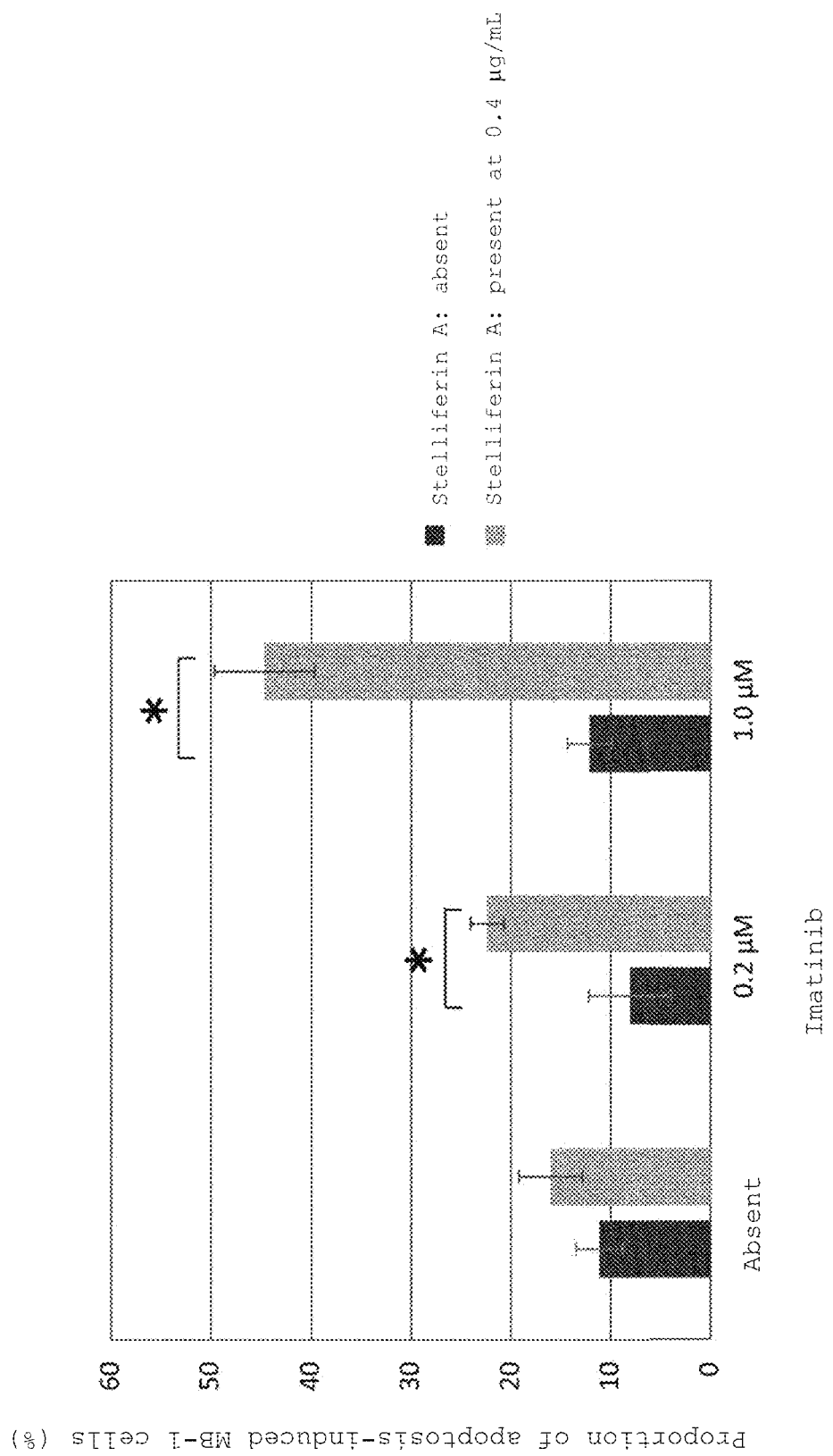

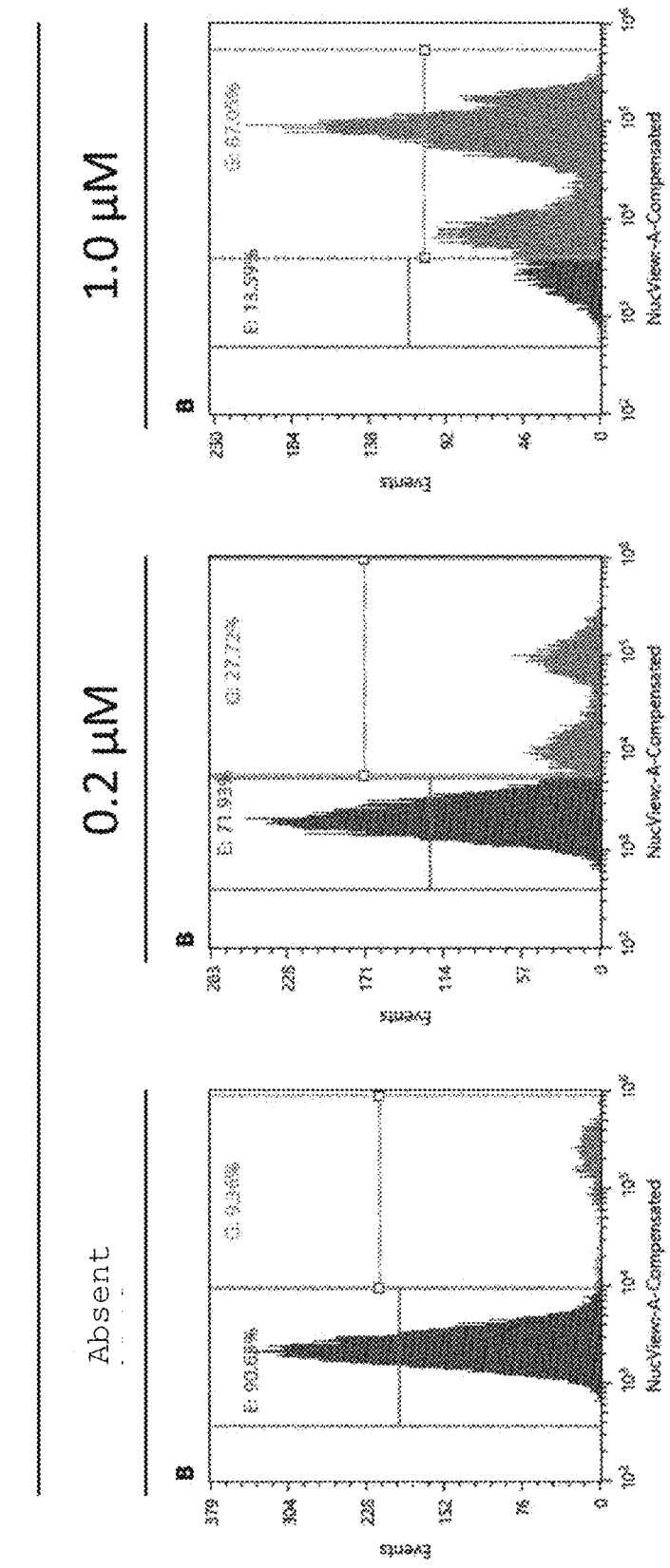
[Figure 11C]

[Figure 12A]
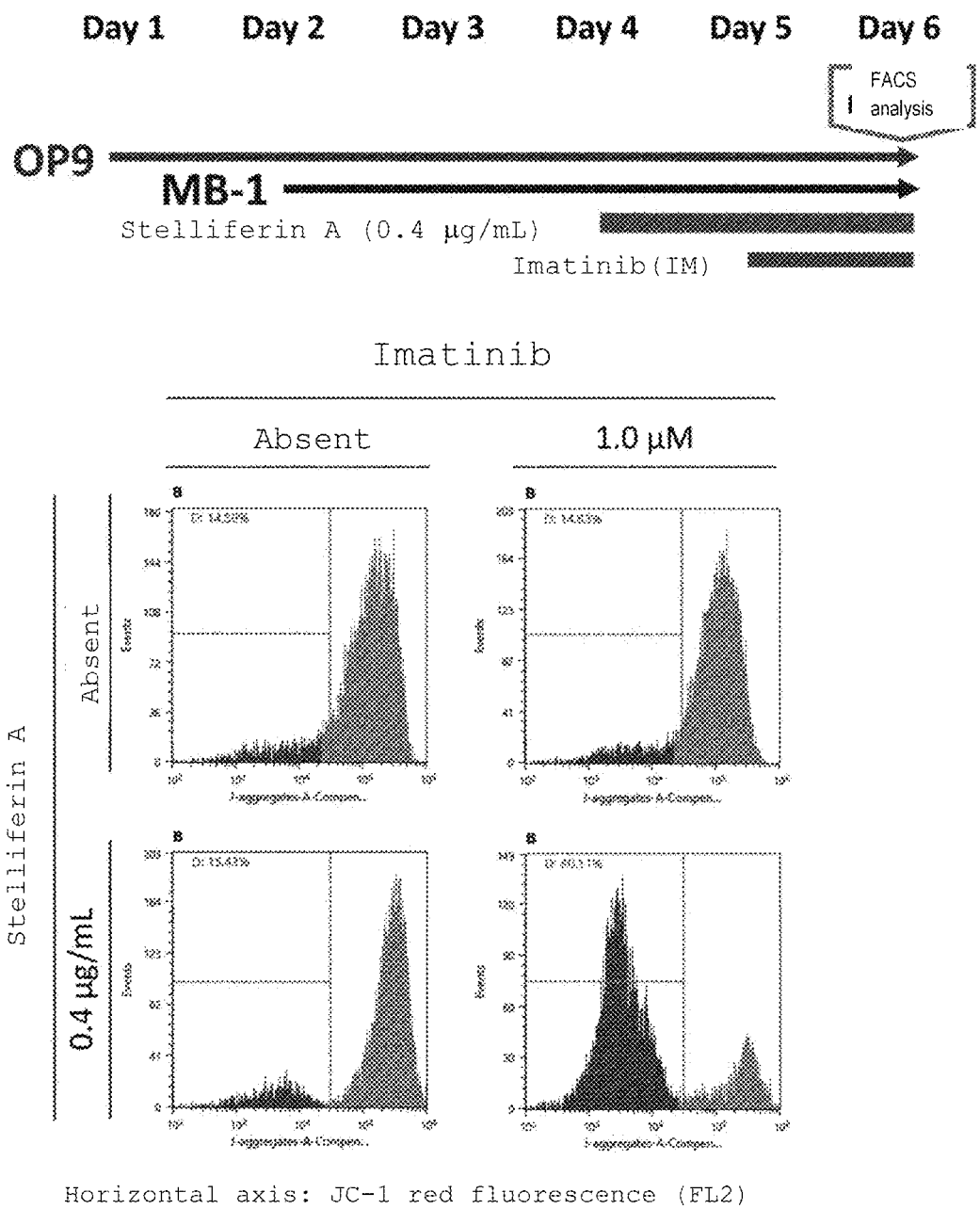
Horizontal axis: JC-1 red fluorescence (FL2)

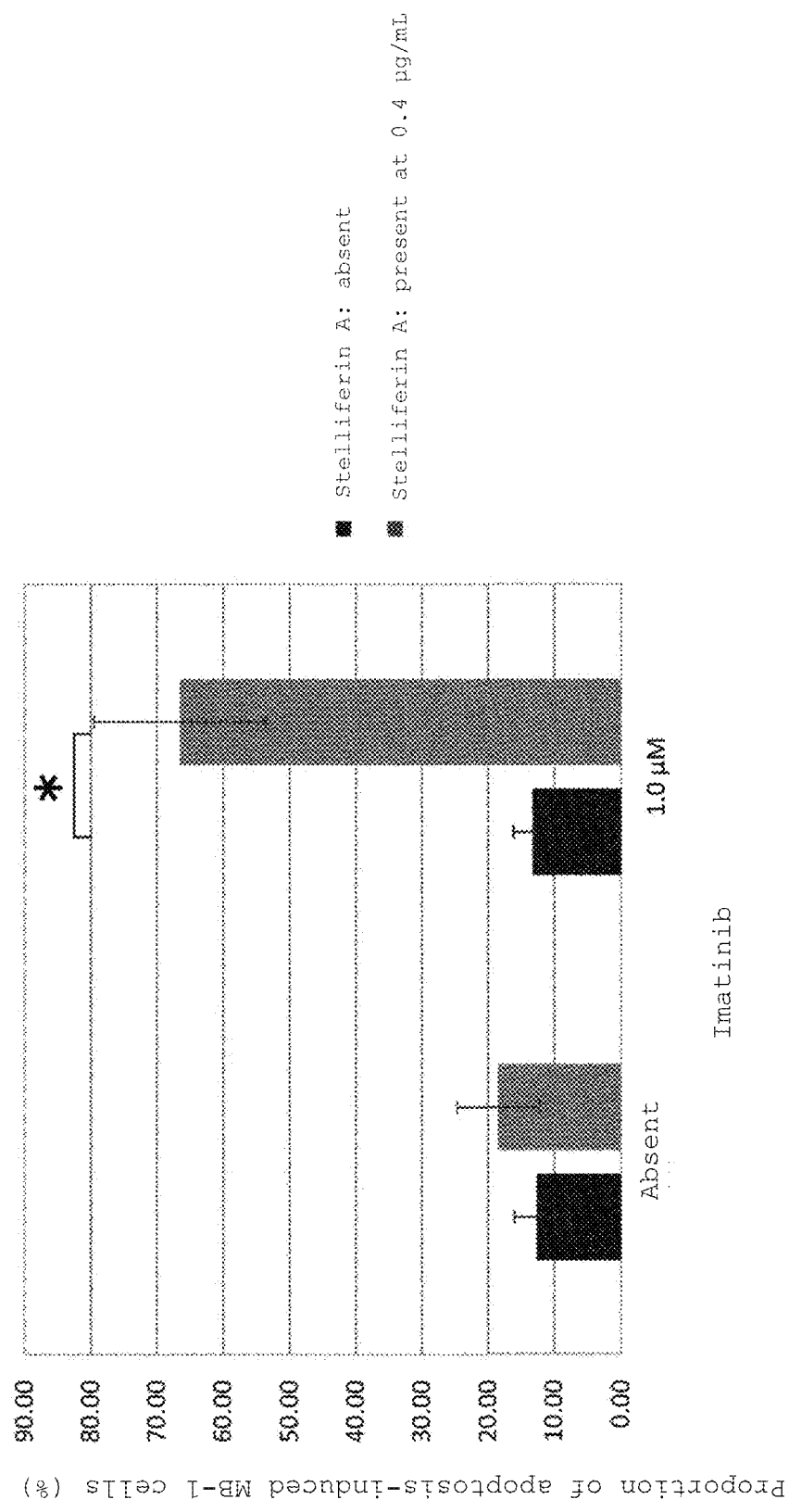
[Figure 12B]

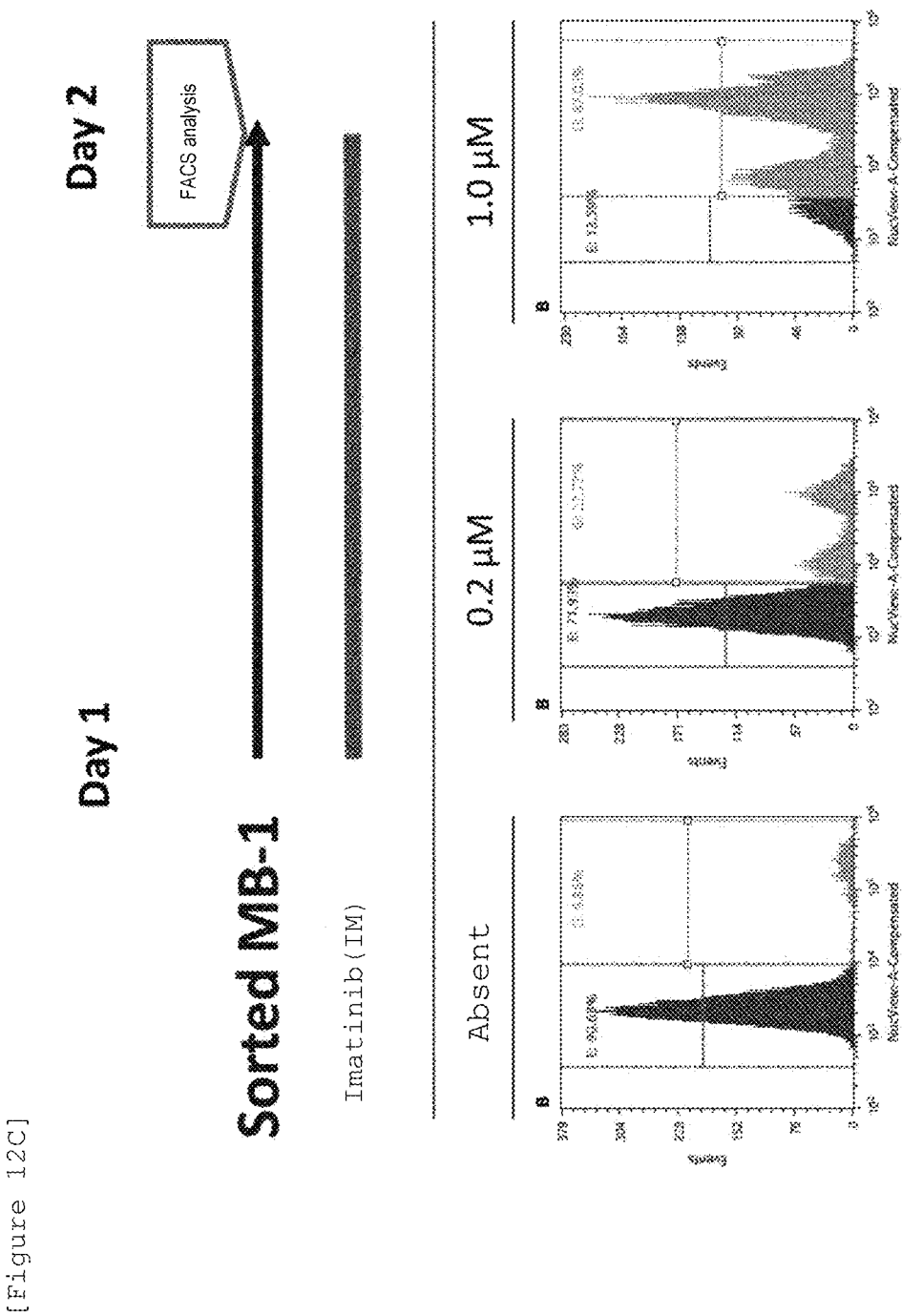
[Figure 12C]

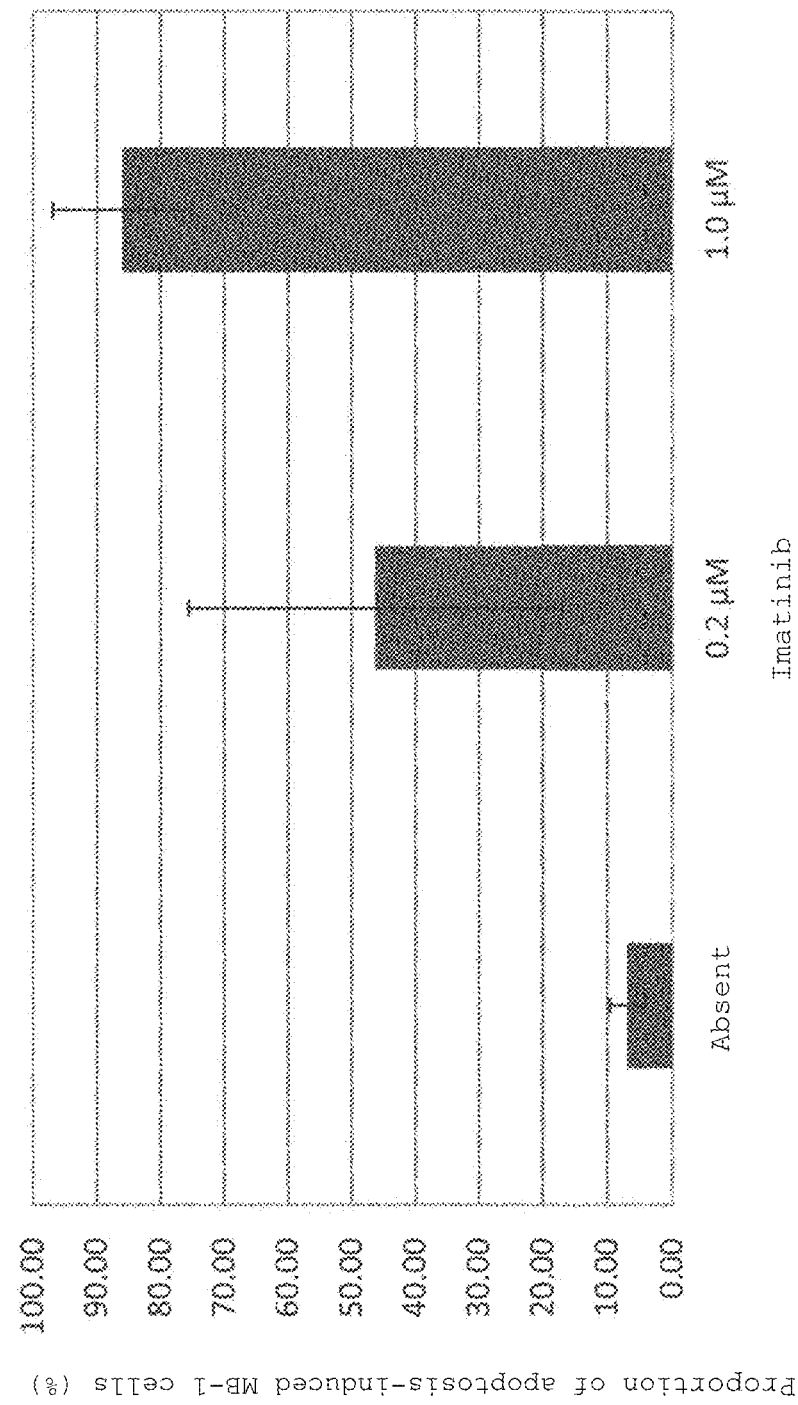
[Figure 12D]

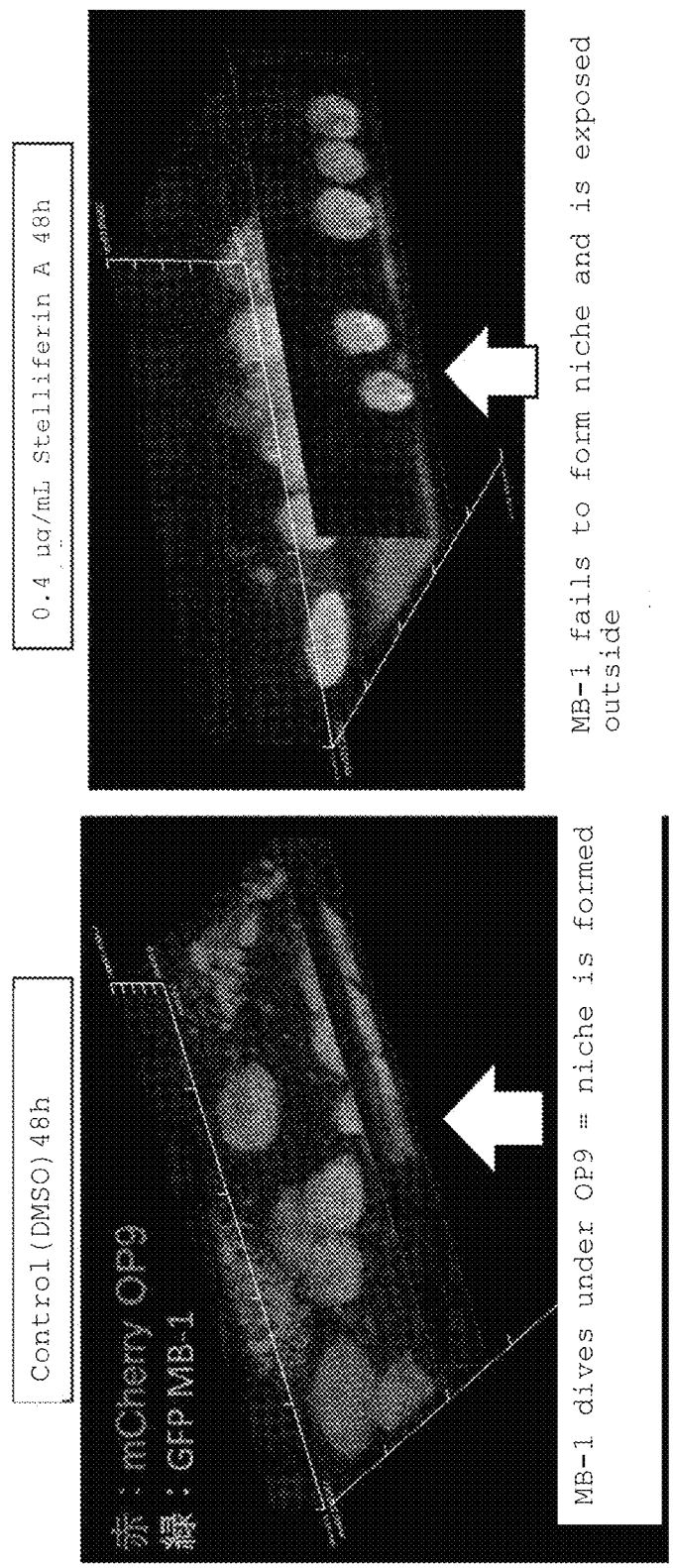
[Figure 13]

[Figure 14A]
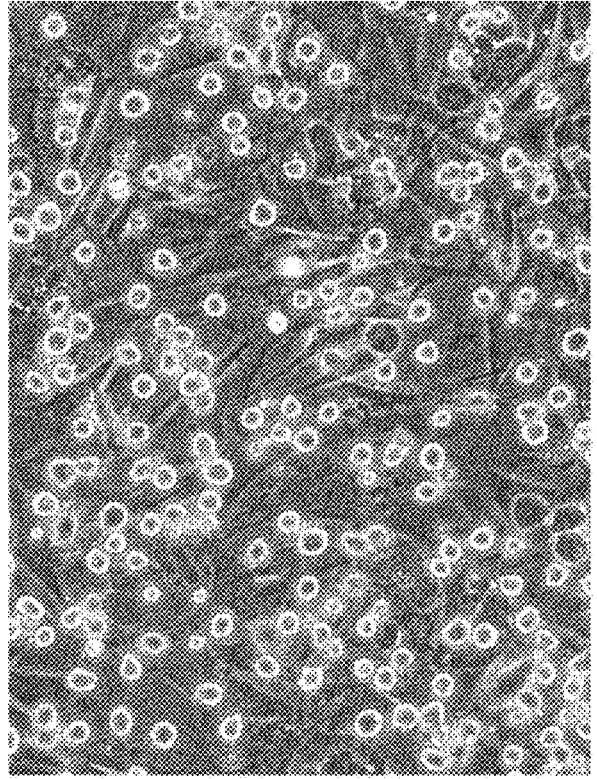
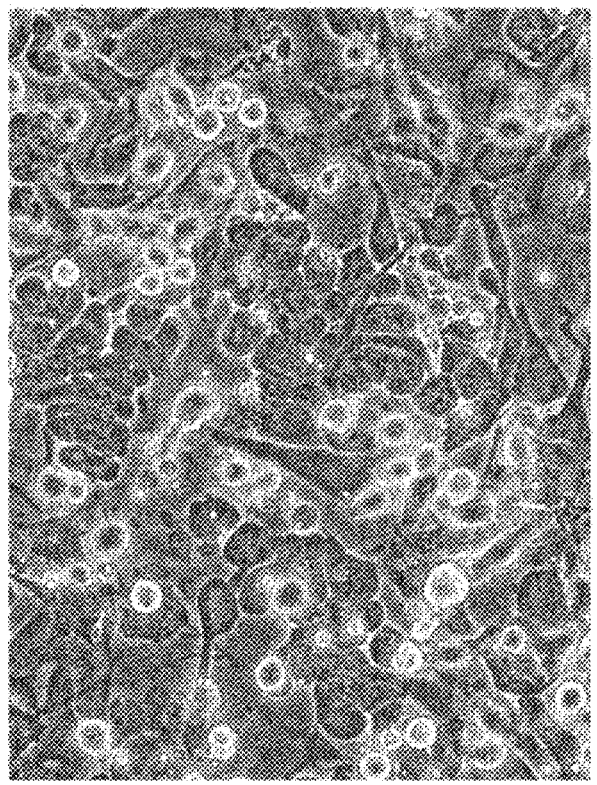

[Figure 14B]
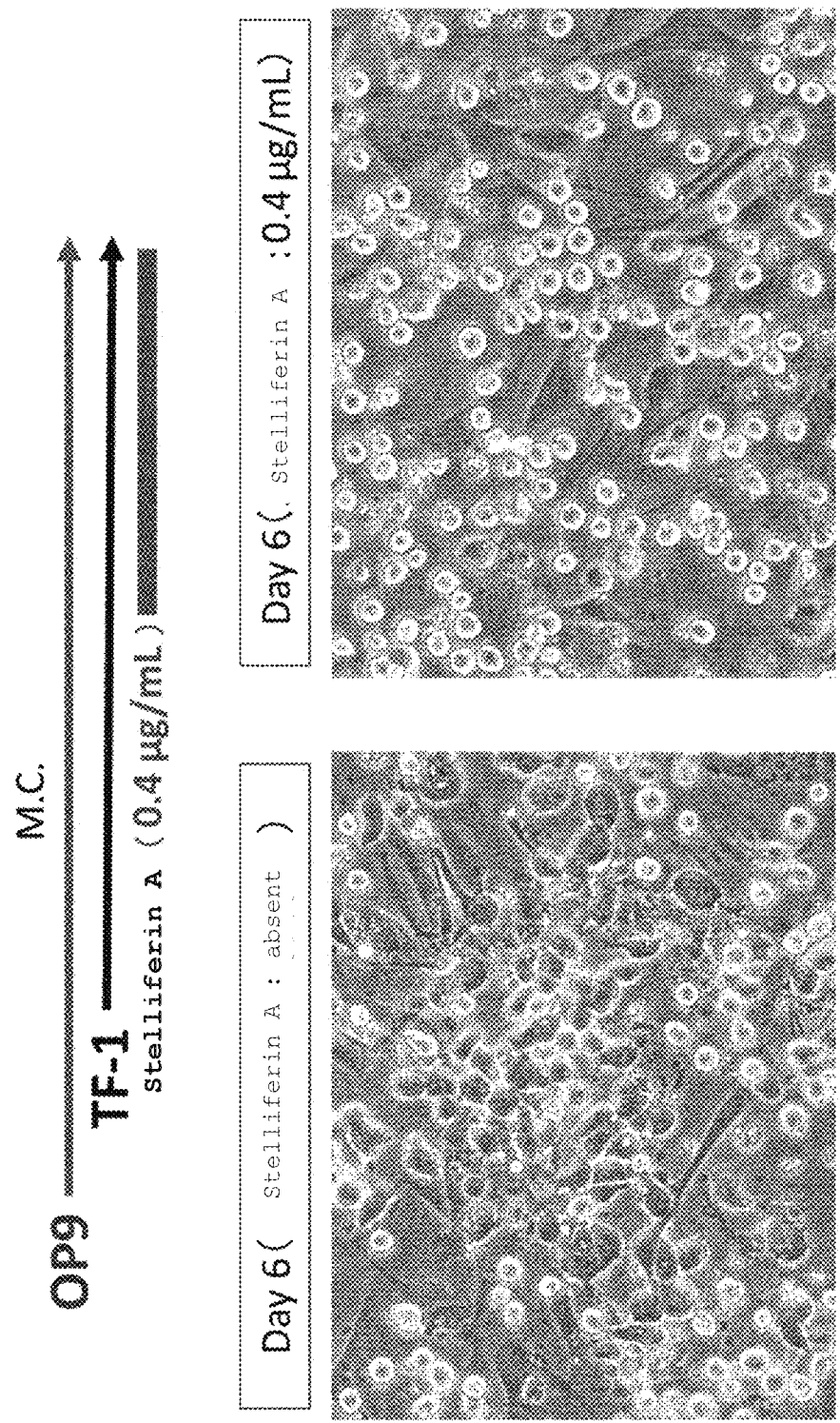

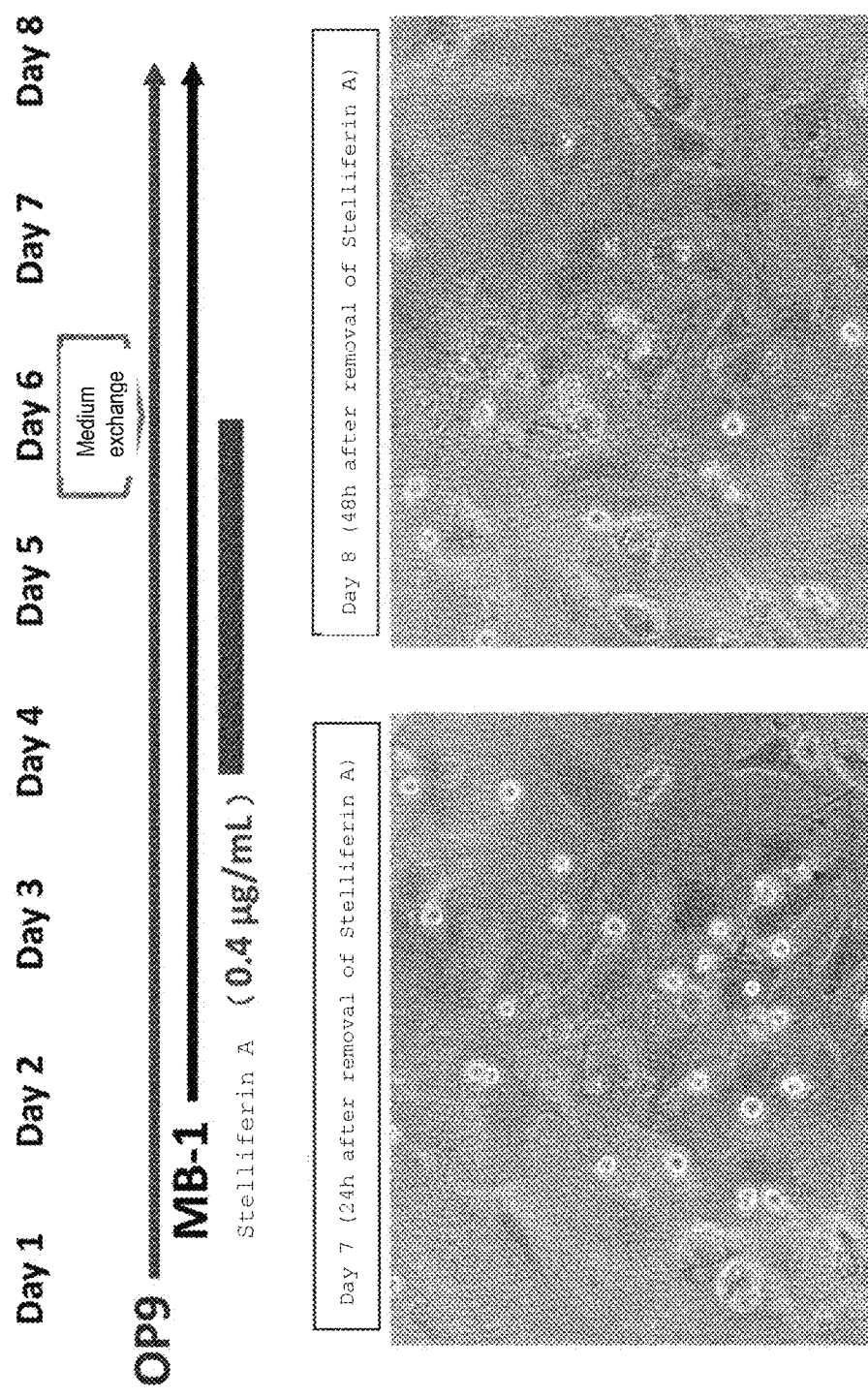

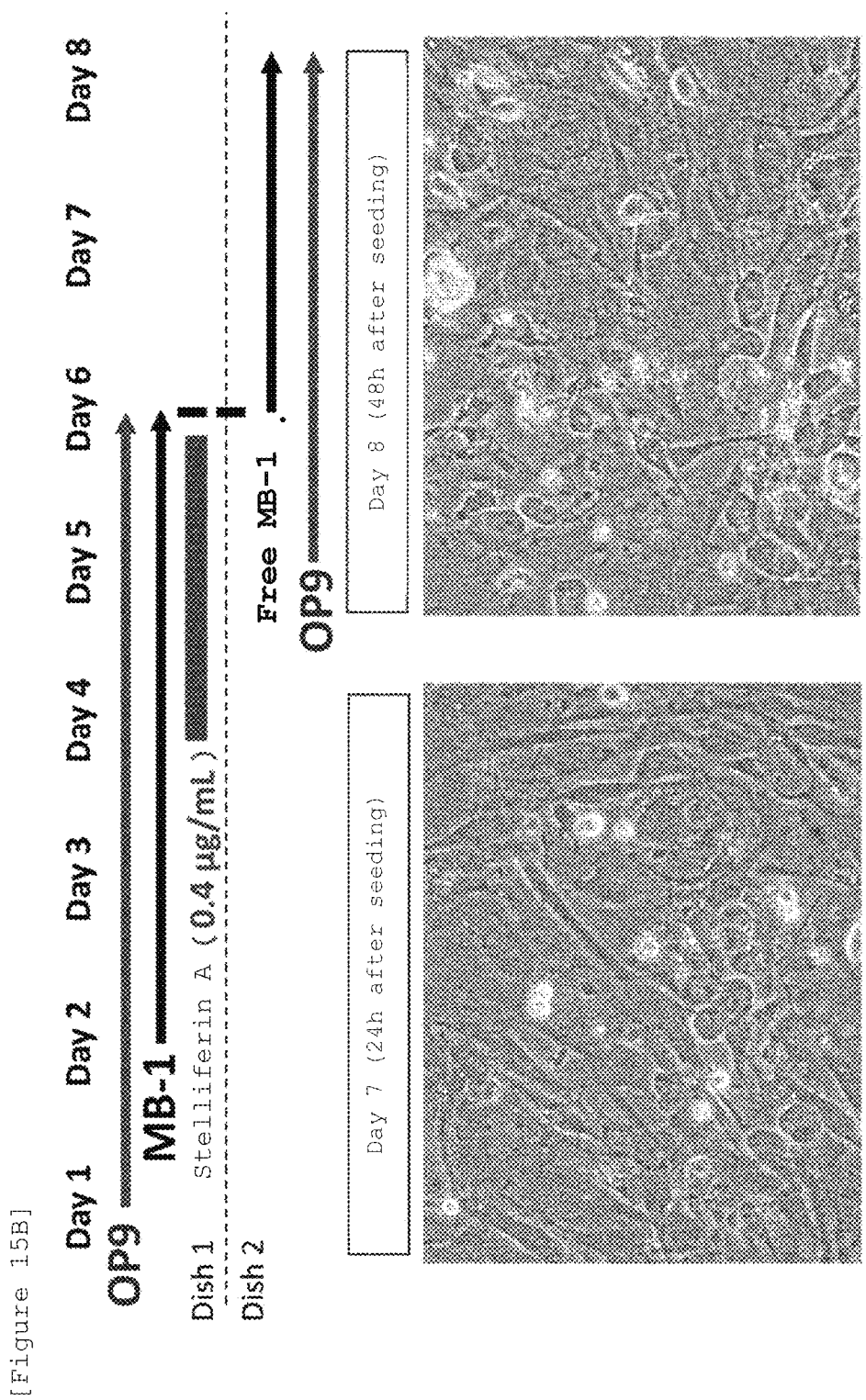

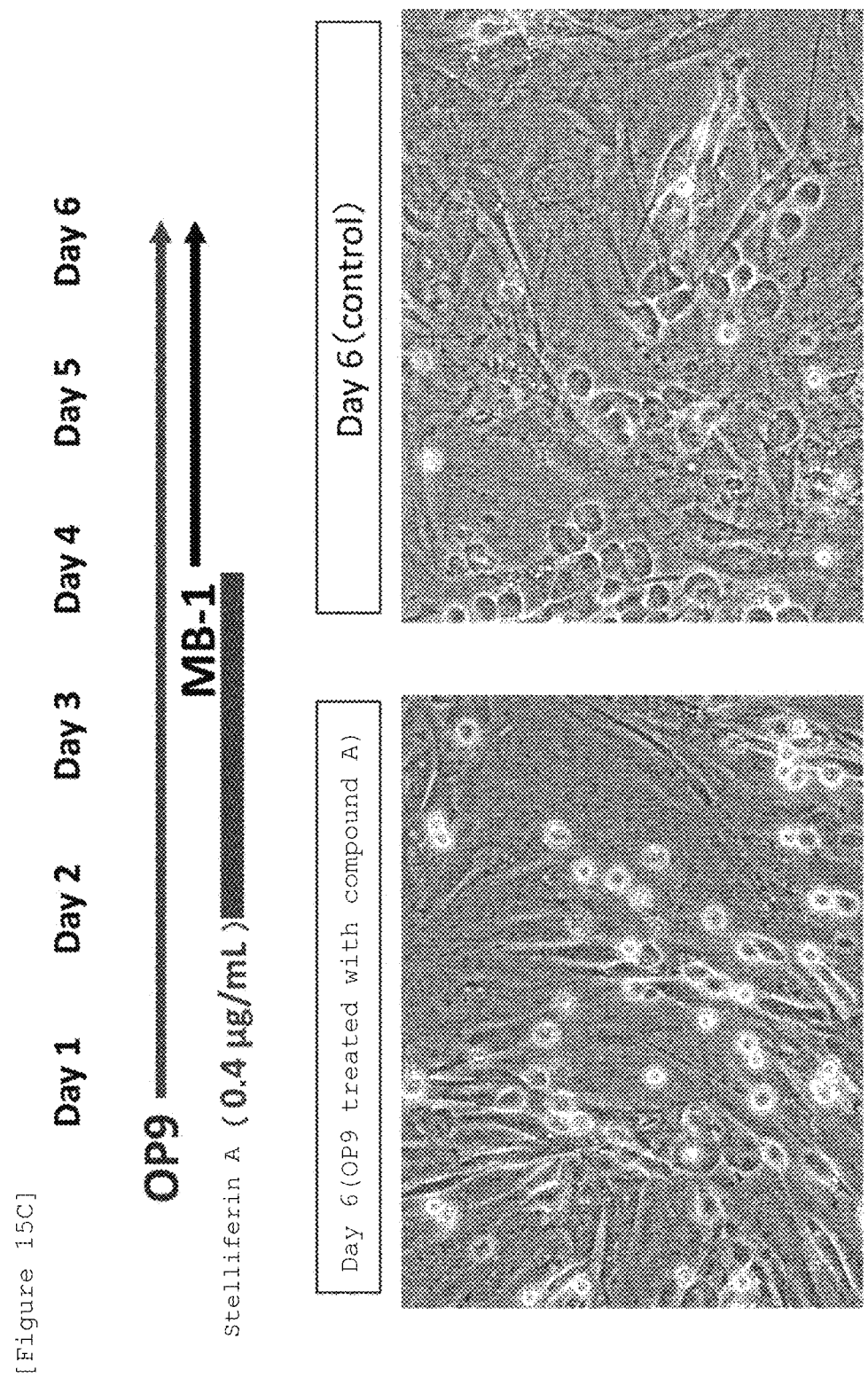

MARINE ORGANISM-DERIVED EXTRACT, COMPOUND, AND MEDICAL COMPOSITION HAVING NICHE FORMATION SUPPRESSING ACTIVITY OF LEUKEMIC STEM CELLS

TECHNICAL FIELD

The present invention relates to: an extract derived from marine organisms, in particular, derived from Porifera, comprising a compound having suppressive activity against the niche formation of leukemic stem cells; a compound isolated and purified from the extract; a derivative thereof; a pharmaceutical composition comprising them; a prophylactic agent against the recurrence of malignant tumor, which is used in combination with other antitumor agents; and a method for separating and/or sorting leukemic stem cells.

BACKGROUND ART

Many antitumor agents including antileukemic agents have been developed and used in clinical sites. These antitumor agents have effects such as suppression of the activity and growth of malignant tumor cells and remission of the symptoms thereof. On the other hand, in many malignant tumors, cancer stem cells having self-replication ability and pluripotency survive and activate, so that malignant tumors have a high recurrence rate. The same is true for leukemia that is also called "cancer of blood," and leukemic stem cells are present also in leukemia. In many cases, such leukemic stem cells remain in a resting stage, in which antitumor agents are hardly effective, and cancer stem cells or leukemic stem cells survive in a "niche" environment. These cells have resistance to drugs, and when the cells activate, they cause recurrence (see FIG. 1).

If the niche environment of leukemic stem cells, the mechanism for forming the niche environment, the mechanism of drug resistance, a method of inhibiting niche formation, etc. are clarified, a drug for targeting the niche formation and suppressing or extinguishing it can be provided. Then, if such a drug for suppressing or distinguishing the niche formation is used in combination with a drug for specifically inducing necrosis or apoptosis to the malignant tumor cells themselves, it is considered that malignant tumors which have been hardly treated by conventional therapeutic methods, such as leukemia, can be completely treated. Thus, a novel drug has been studied as a novel specific therapeutic agent for cancer and/or leukemic stem cells (Patent Literatures 1 to 3).

However, a drug effective for suppressing the tumor cell niche formation of cancer stem cells including leukemic stem cells has not yet been developed.

CITATION LIST

Patent Literature

Patent Literature 1: International Publication No. WO2010/101257
Patent Literature 2: International Publication No. WO2013/009690
Patent Literature 3: International Publication No. WO2013/070807

SUMMARY OF INVENTION

Technical Problem

The present invention provides: an extract comprising a compound having inhibitory or suppressive activity against the niche formation of cancer stem cells, in particular, leukemic stem cells; a compound isolated and purified from the extract; a pharmaceutical composition comprising them; a prophylactic agent against the recurrence of malignant tumor, which is used in combination with other antitumor agents; and a method for separating and/or sorting leukemic stem cells.

Solution to Problem

Using the cobblestone area (CA) formation inhibitory activity of human leukemic stem cell-like cells as an indicator, the present inventors have extracted and separated a fraction having the aforementioned activity from the fat-soluble fraction of Porifera, and thereafter, the inventors isolated and purified a compound having the activity from the aforementioned fraction, and then determined the structure thereof, so that the inventors identified a Stelliferin compound comprising a novel compound. Moreover, the present inventors found that the isolated and purified Stelliferin compound suppresses the niche formation of leukemic stem cell-like cells derived from human chronic myelogenous leukemia (CML) having resistance to existing antitumor agents and enhances the effects of antitumor agents on the cells, thereby completing the present invention.

The present invention provides an extract extracted from Porifera using a fat-soluble solvent, wherein the extract comprises at least 2% (w/w) by dry weight of a Stelliferin compound represented by the following formula (I) and has a suppressive action against the niche formation of tumor cells.

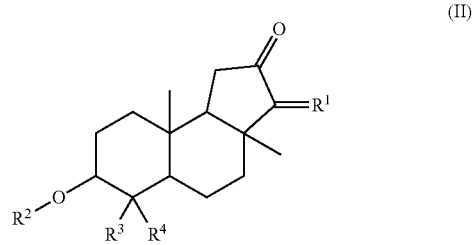

wherein
$R^1$ represents a terpene group,
$R^2$ is selected from the group consisting of H and an acetyl group, and
$R^3$ and $R^4$ are each independently selected from the group consisting of H, —OH, a methyl group, a carboxyl group, and a hydroxymethyl group.

There is a case where the above described extract of the present invention is produced by performing the following steps:

(I) a step of extracting a fat-soluble fraction, using a water-insoluble organic solvent, from an extract, which has been extracted from Porifera using a water-soluble alcohol solvent, (II) a step of adding a high concentration of water-soluble alcohol solvent/aqueous solution and a water-insoluble aliphatic hydrocarbon solvent to the fat-soluble fraction obtained at the step (I) to perform liquid-liquid extraction, so as to recover a water-insoluble aliphatic hydrocarbon solvent layer (fraction 2-1), (III) a step of subjecting the high concentration of water-soluble alcohol solvent/aqueous solution layer in the step (II) to concentration or solvent evaporation, then performing liquid-liquid extraction using an intermediate concentration of water-soluble alcohol solvent/aqueous solution and a chlorinated hydrocarbon solvent, so as to recover a chlorinated hydrocarbon solvent fraction (fraction 2-2), and (IV) a step of subjecting the fraction 2-1 and the fraction 2-2 to concentration or solvent evaporation.

There is a case where the above described extract is an extract produced by performing the following steps:

(I') a step of extracting a fat-soluble fraction according to liquid-liquid extraction using water and a water-insoluble organic solvent, from an extract, which has been extracted from Porifera using a water-soluble alcohol solvent, (II') a step of adding a 90% water-soluble alcohol solvent/aqueous solution and a water-insoluble aliphatic hydrocarbon solvent to the fat-soluble fraction obtained in the step (I') to perform liquid-liquid extraction, so as to recover a water-insoluble aliphatic hydrocarbon solvent layer (fraction 2-1), (III') a step of performing liquid-liquid extraction using a 60% water-soluble alcohol solvent/aqueous solution, which has been diluted by adding water to the 90% water-soluble alcohol solvent/aqueous solution layer in the step (II'), and a chlorinated hydrocarbon solvent, so as to recover a chlorinated hydrocarbon solvent fraction (fraction 2-2), and (IV') a step of subjecting the fraction 2-1 and the fraction 2-2 to concentration or solvent evaporation.

There is a case where, in the method for producing the extract of the present invention, the above described steps (I) to (IV) include the following steps (i) to (v):

(i) a step of performing liquid-liquid extraction on the extract extracted from Porifera using a water-soluble alcohol solvent, using water and a chlorinated hydrocarbon solvent, so as to recover a chlorinated hydrocarbon solvent fraction, (ii) a step of performing liquid-liquid extraction on the water-soluble fraction obtained in the step (i) using a water-insoluble alcohol solvent, (iii) a step of mixing the chlorinated hydrocarbon solvent layer obtained in the step (i) with the water-insoluble alcohol solvent layer obtained in the step (ii), followed by concentration or solvent evaporation, then adding a high concentration of water-soluble alcohol solvent aqueous solution and a water-insoluble aliphatic hydrocarbon solvent to the resultant, and then subjecting the obtained mixture to liquid-liquid extraction, so as to recover a water-insoluble aliphatic hydrocarbon solvent layer, (iv) a step of performing liquid-liquid extraction using an intermediate concentration of water-soluble alcohol solvent/aqueous solution, which has been diluted by adding water to the high concentration of water-soluble alcohol solvent/aqueous solution layer obtained in the step (iii) and a chlorinated hydrocarbon solvent, so as to recover a chlorinated hydrocarbon solvent fraction, and (v) a step of subjecting each fraction of the water-insoluble aliphatic hydrocarbon solvent layer of the step (iii) and the chlorinated hydrocarbon solvent layer of the step (iv) to concentration or solvent evaporation.

There is a case where, in the method for producing the extract of the present invention, the above described steps (I) to (IV) or steps (I') to (IV') include the following steps (i') to (v'):

(i') a step of performing liquid-liquid extraction on the extract extracted from Porifera using a water-soluble alcohol solvent, using water and a chlorinated hydrocarbon solvent, so as to recover a chlorinated hydrocarbon solvent fraction, (ii') a step of performing liquid-liquid extraction on the water-soluble fraction obtained in the step (i) using a water-insoluble alcohol solvent, (iii') a step of mixing the chlorinated hydrocarbon solvent layer in the step (i') with the water-insoluble alcohol solvent layer in the step (ii'), followed by concentration or solvent evaporation, then adding a 90% water-soluble alcohol solvent aqueous solution and a water-insoluble aliphatic hydrocarbon solvent to the resultant, and then subjecting the obtained mixture to liquid-liquid extraction, so as to recover a water-insoluble aliphatic hydrocarbon solvent layer, (iv') a step of performing liquid-liquid extraction using a 60% water-soluble alcohol solvent/aqueous solution, which has been diluted by adding water to the 90% water-soluble alcohol solvent/aqueous solution in the step (iii'), and a chlorinated hydrocarbon solvent, so as to recover a chlorinated hydrocarbon solvent fraction, and (v') a step of subjecting each fraction of the water-insoluble aliphatic hydrocarbon solvent layer of the step (iii') and the chlorinated hydrocarbon solvent layer of the step (iv') to concentration or solvent evaporation.

There is a case where the method for producing the above described extract of the present invention further comprises the following steps (vi) to (viii), in addition to the above described steps (I) to (IV), (I') to (IV'), (i) to (v), or (i') to (v'), and the above described extract of the present invention comprises 70% or more of a Stelliferin compound:

(vi) a step of successively eluting a fat-soluble fraction extracted with the fat-insoluble aliphatic hydrocarbon solvent described in the step (IV), (IV'), (v) or (v'), according to silica gel column chromatography, using a non-polar solvent, a mixed solvent of a non-polar solvent and a polar solvent, and further, using a mixed solvent of a polar solvent and water in this order, so as to obtain a fraction having suppressive action against the niche formation of tumor cells, (vii) a step of purifying the fat-soluble fraction, before or after the step (vi), optionally, according to ODS reverse phase high performance liquid chromatography, by gradient chromatography using a mixed solvent of methanol and water, so as to obtain a fraction having suppressive action against the niche formation of tumor cells, and (viii) a step of further fractionating the fraction having suppressive action against the niche formation of tumor cells obtained in the step (vi) or (vii) according to high performance liquid chromatography.

The conditions for fractionating the fraction according to high performance liquid chromatography in the step (viii) may be the following conditions in some cases.

(a) The following conditions are applied to ODS reverse phase high performance liquid chromatography:
Solid phase: COSMOSIL® 5C18 AR II
Solid phase size: 10 mm in inner diameter×250 mm in length
Mobile phase: 80% methanol aqueous solution
Flow rate: 2.0 mL/min.

A fraction obtained at a retention time of 30 minutes or 34 minutes is recovered, and then, a step of subjecting the fraction obtained at a retention time of 30 minutes to solvent evaporation is performed to obtain an extract comprising 70% or more of a Stelliferin compound, or a step of subjecting the fraction obtained at a retention time of 34 minutes to solvent evaporation is performed to obtain an extract comprising 70% or more of a Stelliferin compound.

Otherwise, (b) the following conditions are applied to ODS reverse phase high performance liquid chromatography:
Solid phase: COSMOSIL® 5C18 AR II
Solid phase size: 10 mm in inner diameter×250 mm in length
Mobile phase: 85% methanol aqueous solution
Flow rate: 2.0 mL/min.

A step of subjecting the fraction obtained at a retention time of 40-42 minutes to solvent evaporation is performed to obtain an extract.

In the invention of the extract, the Stelliferin compound may be selected from the group consisting of Stelliferin A, Stelliferin B, and a diastereomer or enantiomer thereof in some cases.

In the above described extract of the present invention, the tumor cells may be cancer stem cells, leukemic stem cells, or chronic myelogenous leukemic cells in some cases.

Moreover, the present invention provides a compound represented by the following formula (II):

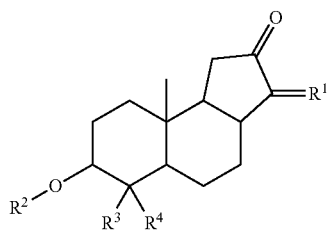

(II)

wherein $R^1$ is selected from the group consisting of the following formula (III), formula (IV), and a terpene group,

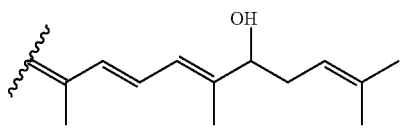

(III)

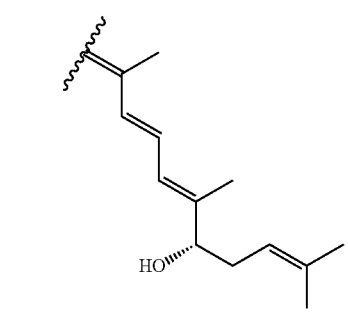

(IV)

$R^2$ is selected from the group consisting of H, —COCH$_3$, —COCH$_2$CH$_3$, —CO(CH$_2$)$_2$CH$_3$, μCOCH(CH$_3$)$_2$, and —COC(CH$_3$)$_3$, or a pharmaceutically acceptable salt thereof.

With regard to the above described compound of the present invention, the compounds represented by the above formulae (I) to (IV) may be represented by the following formulae (V) to (VII) in some cases:

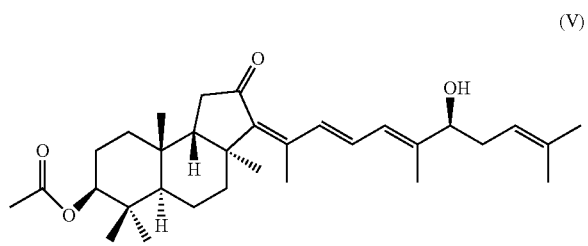

(V)

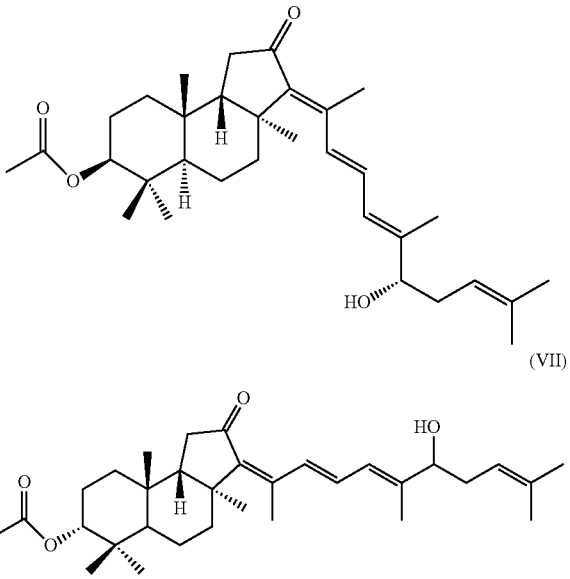

(VI)

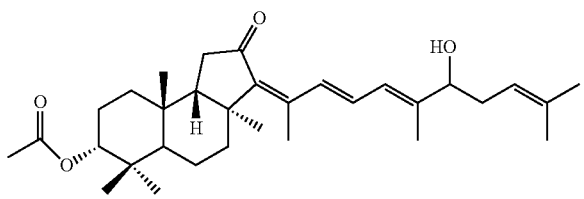

(VII)

Furthermore, the present invention provides an inhibitor against the niche formation of tumor cells, comprising the above described extract or the above described compound.

There is a case where the present invention relates to a method for preventing and/or treating the niche formation of tumor cells, comprising administering an effective dose of the above described extract or the above described compound to a patient in need thereof.

In addition, the present invention provides the above described extract or the above described compound for use in the method for preventing and/or treating the niche formation of tumor cells.

Moreover, the present invention provides a use of the above described extract or the above described compound for the production of a drug for preventing and/or treating the niche formation of tumor cells.

Furthermore, the present invention provides an inhibitor against the niche formation of tumor cells, comprising the above described extract, the above described compound, or a pharmaceutically acceptable salt thereof.

Further, the present invention provides a method for preventing and/or treating the niche formation of tumor cells, comprising administering an effective dose of the above described extract, the above described compound, or a pharmaceutically acceptable salt thereof to a patient in need thereof.

Still further, the present invention provides the above described extract, the above described compound, or a pharmaceutically acceptable salt thereof, for use in a method for preventing and/or treating the niche formation of tumor cells.

Still further, the present invention provides use of the above described extract, the above described compound, or a pharmaceutically acceptable salt thereof, for the production of a drug for preventing and/or treating the niche formation of tumor cells.

In the methods and uses of the present invention involving the above described inhibitor against niche formation, or the above described extract or the above described compound having the inhibitory action against niche formation, there is a case where the tumor cells are cancer stem cells, leukemic stem cells, or chronic myelogenous leukemic cells.

Moreover, the present invention provides an antitumor pharmaceutical composition, in which the above described extract or the above described compound is combined with one or two or more antitumor agents.

Furthermore, the present invention provides a method for preventing and/or treating tumor, comprising administering, to a patient in need thereof, an effective dose of the above described extract or the above described compound, which is combined with one or two or more antitumor agents.

Further, the present invention provides the above described extract or the above described compound, which is combined with one or two or more antitumor agents and is used in a method for preventing and/or treating tumor.

Still further, the present invention provides use of the above described extract or the above described compound, which is combined with one or two or more antitumor agents and is used in the production of a medicament for preventing and/or treating tumor.

With regard to the antitumor pharmaceutical composition, there is a case where the above described antitumor agent is at least one selected from the group consisting of ibritumomab tiuxetan, imatinib, erlotinib, gefitinib, gemtuzumab ozogamicin, sunitinib, cetuximab, sorafenib, dasatinib, tamibarotene, trastuzumab, tretinoin, panitumumab, bevacizumab, bortezomib, lapatinib, rituximab, ifosfamide, cyclophosphamide, dacarbazine, temozolomide, nimustine, busulfan, melphalan, enocitabine, capecitabine, carmofur, gemcitabine, cytarabine, tegafur, tegafur-uracil, nelarabine, fluorouracil, fludarabine, pemetrexed, pentostatin, methotrexate, irinotecan, etoposide, sobuzoxane, docetaxel, nogitekan, paclitaxel, vinorelbine, vincristine, vindesine, vinblastine, actinomycin D, aclarubicin, idarubicin, epirubicin, daunorubicin, doxorubicin, pirarubicin, bleomycin, peplomycin, mitomycin C, mitoxantrone, oxaliplatin, carboplatin, cisplatin, nedaplatin, anastrozole, exemestane, ethinylestradiol, rorumajinon, goserelin, tamoxifen, bicalutamide, flutamide, prednisolone, leuprorelin, letrozole, interferon α, interferon β, interferon γ, interleukin 2, ubenimex, dried BCG, and lentinan.

There is a case where the above described pharmaceutical composition of the present invention is a prophylactic agent against the recurrence of malignant tumor for use in preventing the recurrence of malignant tumor.

In addition, there is a case where the present invention relates to a method for preventing the recurrence of malignant tumor, comprising administering an effective dose of the above described pharmaceutical composition to a patient in need thereof.

Moreover, there is a case where the above described pharmaceutical composition of the present invention is a pharmaceutical composition for use in a method for preventing the recurrence of malignant tumor.

Furthermore, there is a case where the present invention relates to a pharmaceutical composition for use in a method for preventing the recurrence of malignant tumor.

Further, there is a case where the present invention relates to a pharmaceutical composition for use in the production of a medicament for preventing the recurrence of malignant tumor.

Still further, the present invention provides a method for separating and/or sorting cancer stem cells or leukemic stem cells, in which the above described extract or the above described compound is used.

Still further, in the present invention, the above described "extract" may also be referred to as a "composition" in some cases.

Effects of Invention

The present invention provides: an extract derived from marine organisms, in particular, derived from marine sponge, comprising a compound having suppressive activity against the niche formation of cancer stem cells including leukemic stem cells; an active compound isolated and purified from the extract; an inhibitor against niche formation, comprising them as active ingredients; a drug for preventing the recurrence of malignant tumor, which is used in combination with other antitumor agents; and a method for separating and/or sorting cancer stem cells or leukemic stem cells.

BRIEF DESCRIPTION OF DRAWINGS

FIG. 1A is an illustration describing the relationship between drug resistance of leukemic stem cells (LSC) and recurrence of leukemia.

FIG. 1B is a photomicrograph of a cobblestone area (CA: niche environment model) produced by co-culturing human chronic myelogenous leukemia (CML)-derived cell strain MB-1 and mouse myeloid-derived interstitial cell strain OP9.

FIG. 2A is a view outlining operations for screening method.

FIG. 2B is a view showing the reference for screening method in determining the presence or absence of cobblestone area (CA) formation.

FIG. 3 is a scheme of separating/purifying fat-soluble fractions 2-1 and 2-2, which are fractioned from Porifera (scientific name: *Stelleta globostellata*, code number S12111) obtained in Kakeromajima and have a suppressive action against the formation of a niche by MB-1 cells.

FIG. 4 shows photographs showing CA formation inhibitory action by the S12111 fraction (fat-soluble fraction).

FIG. 5 shows a scheme of further separating isolating/purifying fat-soluble fraction 2-1 into fraction 10-3 and fraction 10-5 having a niche formation suppressive action by MB-1 cells.

FIG. 6 shows a scheme of separating/purifying fraction 9-2 having a niche formation suppressive action by MB-1 cells from Porifera (scientific name: *Stelleta globostellata*, code number: S09226) obtained in Mageshima.

FIG. 7A shows a chromatogram obtained by fractionating fraction 9-2, which is fractionated from S09226 fraction, into fractions 15-1 to 15-10, by liquid chromatography.

FIG. 7B shows the amounts of individual fractions 15-1 to 15-10 obtained by fractionating fraction 9-2 by liquid chromatography.

FIG. 8 shows the NMR measurement results of a compound in fraction 10-3 isolated/purified from S12111 fraction and identification of the structural formula thereof.

FIG. 9 shows the NMR measurement results of a compound in fraction 10-5 isolated/purified from S12111 fraction and identification of the structural formula thereof.

FIG. 10A shows a mass spectrum of a compound in fraction 15-4 isolated/purified from S09226 fraction.

FIG. 10B shows NMR measurement results of a compound in fraction 15-4 isolated/purified from S09226 fraction and identification of the structural formula thereof.

FIG. 11A shows FACS charts showing apoptosis inducing action of Stelliferin A and imatinib on MB-1 cells, which was evaluated by adding Stelliferin A and imatinibs different in concentration to a co-culture system of MB-1 cells (chronic myelogenous leukemic cells) and OP9 cells and using a nuclear-staining fluorescent reagent, NucView 488.

FIG. 11B is a graph numerically summarizing the FACS results of apoptosis inducing action of Stelliferin A and imatinib, which was evaluated by adding Stelliferin A and imatinibs different in concentration to a co-culture system of MB-1 cells (chronic myelogenous leukemic cells) and OP9 cells and using a nuclear-staining fluorescent reagent, NucView 488.

FIG. 11C shows charts indicating dose-dependent apoptosis inducing action of imatinib in a culture system of MB-1 cells alone evaluated by using nuclear-staining fluorescent reagent, NucView 488.

FIG. 12A shows FACS charts showing apoptosis inducing action of Stelliferin A and imatinib on MB-1 cells, which was evaluated by adding Stelliferin A and imatinib to a co-culture system of MB-1 cells (chronic myelogenous leukemic cells) and OP9 cells and using fluorescent reagent JC-1 detecting mitochondrial membrane potential difference.

FIG. 12B is a graph numerically summarizing the FACS results of the apoptosis inducing action of Stelliferin A and imatinib on MB-1 cells, which was analyzed by adding Stelliferin A and imatinib to a co-culture system of MB-1 cells (chronic myelogenous leukemic cells) and OP9 cells and staining with JC-1 reagent.

FIG. 12C shows FACS charts indicating the apoptosis inducing action of Stelliferin A and imatinib on MB-1 cells, which was evaluated by adding Stelliferin A and imatinibs different in concentration to a co-culture system of MB-1 cells (chronic myelogenous leukemic cells) and OP9 cells and staining with JC-1 reagent.

FIG. 12D is a graph numerically summarizing the FACS results of the apoptosis inducing action of Stelliferin A and imatinib on MB-1 cells, which was evaluated by adding Stelliferin A and imatinibs different in concentration to a co-culture system of MB-1 cells (chronic myelogenous leukemic cells) and OP9 cells and staining with JC-1 reagent.

FIG. 13 shows the stereoscopic positional relationship between OP9 cells and MB-1 cells, which was examined by introducing fluorescent proteins (mCherry and GFP) genes in OP9 cells and MB-1 cells, respectively, and using a confocal microscope.

FIG. 14A shows photomicrographs showing a suppressive action against a niche formation of S12111 fraction, which was evaluated in a co-culture system of TF-1 cells having leukemic stem-cell-like characteristic and OP9 cells.

FIG. 14B shows photomicrographs showing a suppressive action against a niche formation of Stelliferin A, which was evaluated in a co-culture system of TF-1 cells and OP9 cells.

FIG. 15A shows the CA formation inhibitory activity of Stelliferin A, which was evaluated by co-culturing MB-1 cells and OP9 cells in the presence of Stelliferin A and then removing Stelliferin A.

FIG. 15B shows the effect of Stelliferin A on inhibition of CA formation, which was evaluated by co-culturing MB-1 cells and OP9 cells in the presence of Stelliferin A, collecting free MB-1 cells, and then co-culturing the MB-1 cells and fresh OP9 cells in the absence of Stelliferin A.

FIG. 15C shows the CA formation inhibitory action of Stelliferin A, which was evaluated by culturing OP9 cells in the presence of Stelliferin A and then co-culturing the OP9 cells and MB-1 cells in the absence of Stelliferin A.

DESCRIPTION OF EMBODIMENTS

One embodiment of the present invention is an extract extracted from Porifera using a fat-soluble solvent/wherein the extract comprises at least 2% (w/w) by dry weight of a Stelliferin compound based on the total dry weight of the above described extract, and has suppressive activity against the niche formation of tumor cells.

In the present description, the Stelliferin compound means a compound represented by the following formula (VIII):

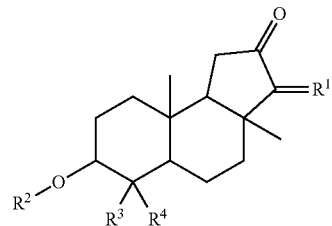

wherein
$R^1$ represents a terpene group,
$R^2$ is selected from the group consisting of H or a $C_{1-4}$ acyl group, and is preferably selected from the group consisting of H and an acetyl group, and
$R^3$ and $R^4$ are each independently selected from the group consisting of H, —OH, a $C_{1-6}$ alkyl group which is preferably a methyl group, a hydroxyalkyl group which is preferably a hydroxymethyl group, a carboxyl group, and an ester derivative thereof.

Examples of the above described terpene group include substituents represented by the following formulae (1) to (45):

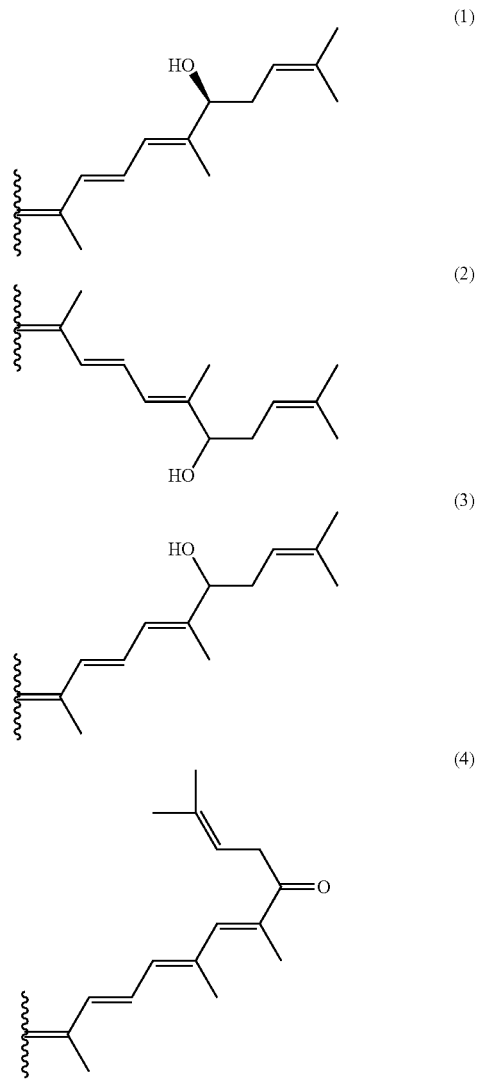

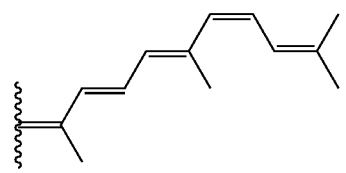
(5)
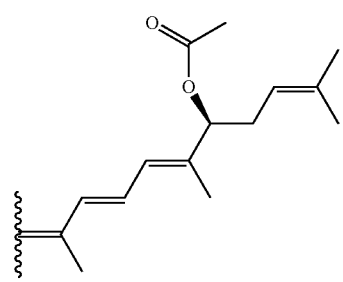
(6)
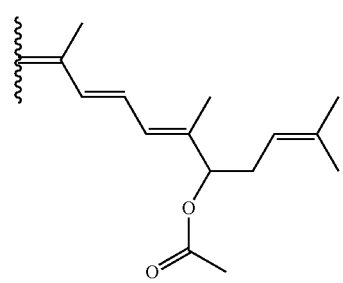
(7)
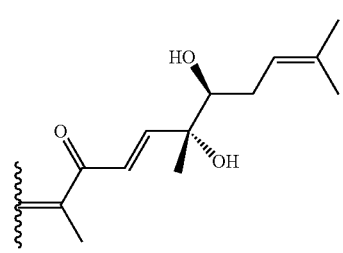
(8)
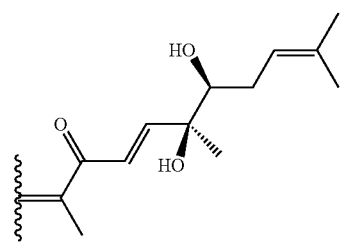
(9)
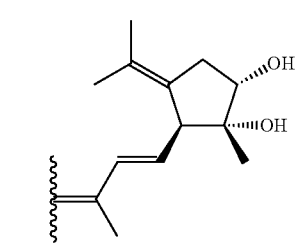
(10)
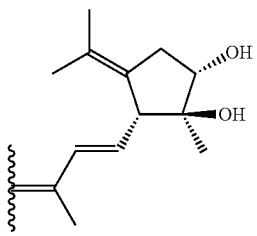
(11)
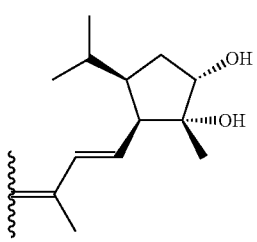
(12)
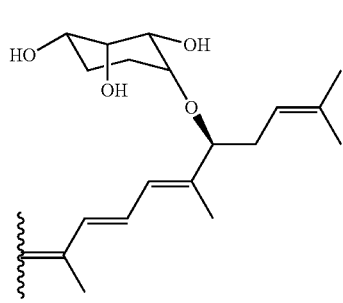
(13)
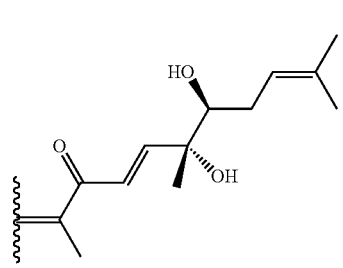
(14)
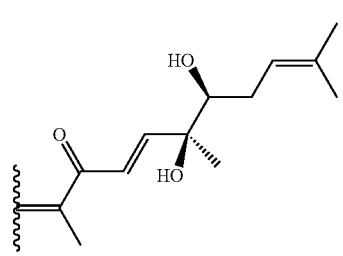
(15)
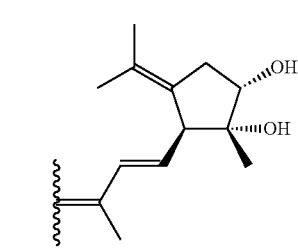
(16)

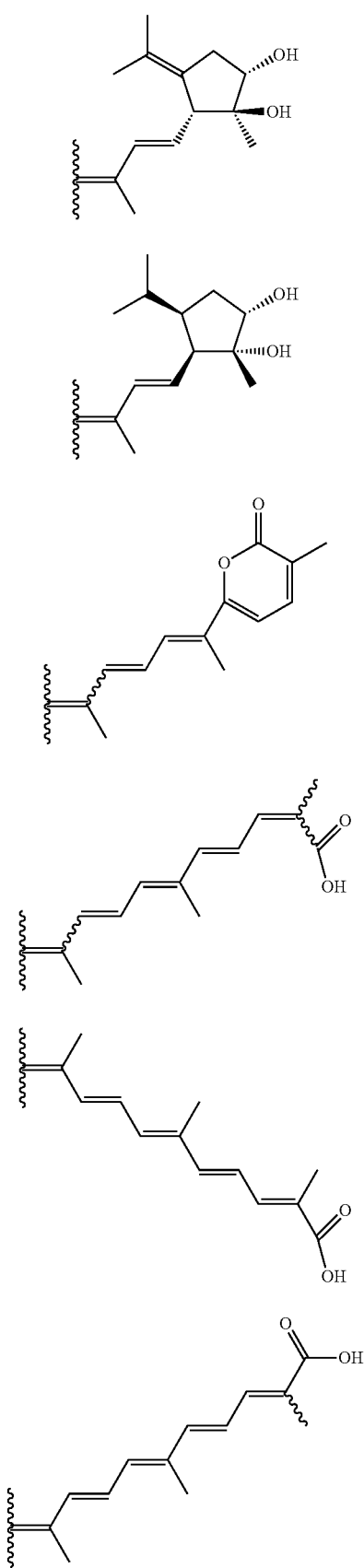
(17)
(18)
(19)
(20)
(21)
(22)
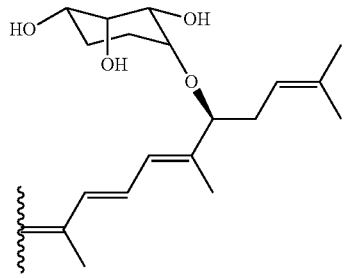
(23)
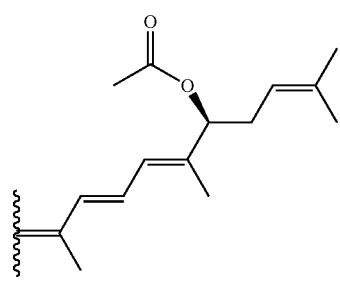
(24)
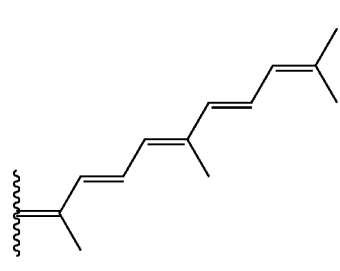
(25)
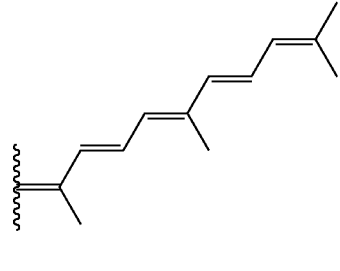
(26)
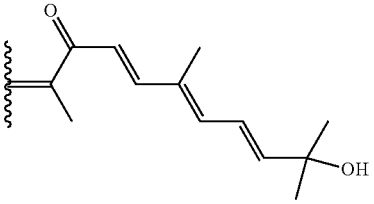
(27)
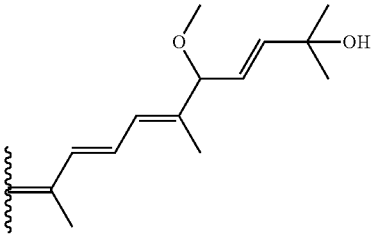
(28)

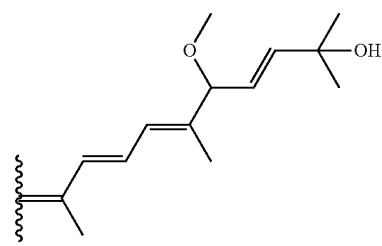
(29)
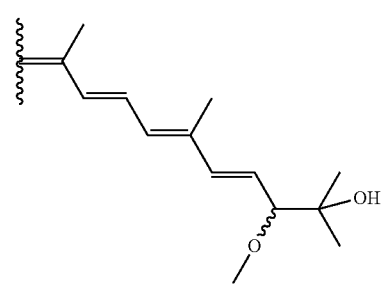
(30)
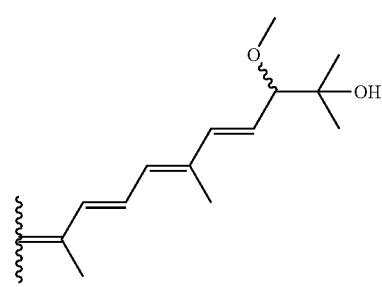
(31)
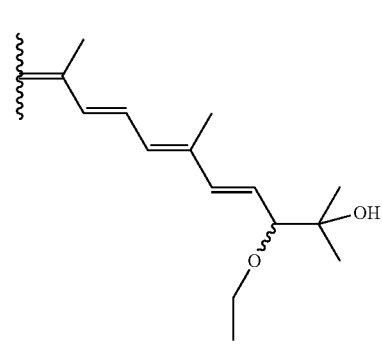
(32)
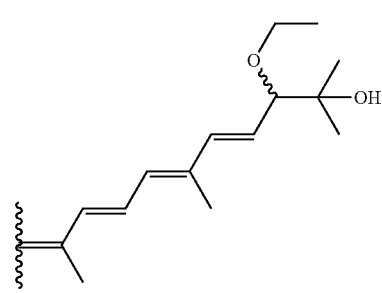
(33)
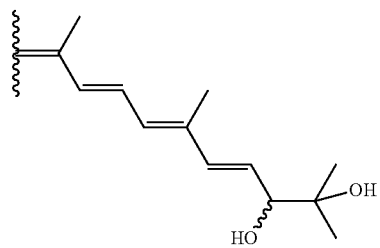
(34)
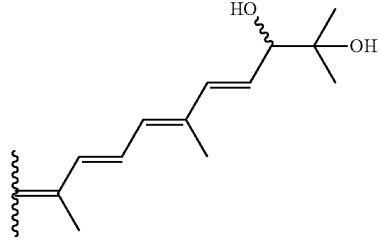
(35)
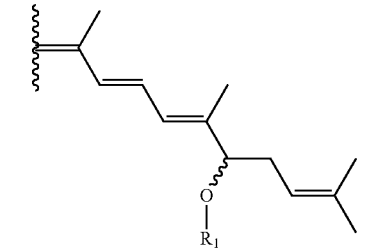
(36)
$R_1$ = ribose
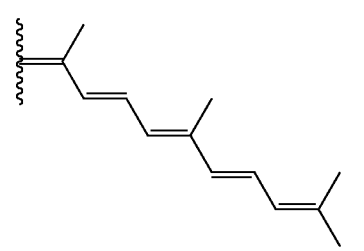
(37)
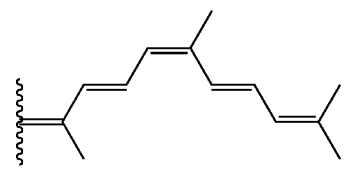
(38)
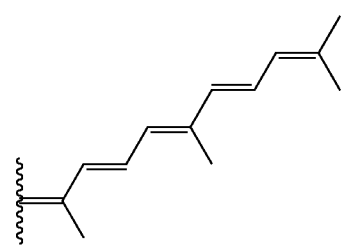
(39)
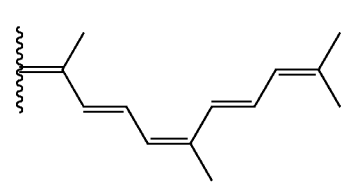
(40)

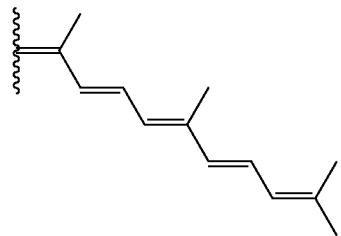
(41)

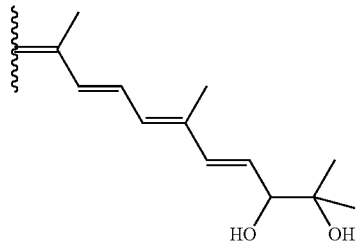
(42)

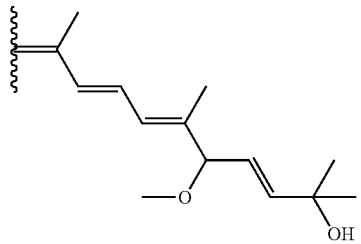
(43)

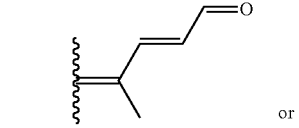
(44)

or

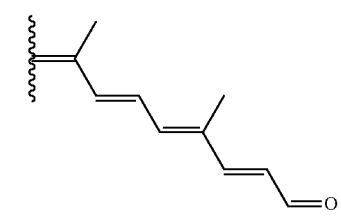
(45)

Among Stelliferin compounds having the terpene groups of the above formulae (1) to (45), in terms of the structural formulae thereof, methods of obtaining them, etc., Stelliferins A to F are described in Tsuda M. et al., Symposium on the Chemistry of Natural Products, Symposium Paper 33, 441-447 (Sep. 7, 1991); Stelliferins J to N are described in Tanaka N. et al., Tetrahedron, Vol. 67, 6689-6696 (2011); Stellettins A to are described in McCormick, J. L. J. Nat. Prod. 59: 1047-1050 (1996) and Tang S.-A, et al., Chinese J. Nat. Med. 3: 213-218 (2005); globostellatic acids A to D are described in Ryu G. et al., J. Nat. Prod., 59: 512-514 (1996); globostellatic acid, globostellatic acids A, D and F to M, 13E-isomer of stelliferin riboside, stelliferin riboside and 3-O-deacetyl-13Z-stelliferin riboside are described in Fouad M et al., J. Nat. Prod., 69: 211-218 (2006); and globostellatic acid X methyl esters are described in Aoki S. et al., Bioorg Med Chem. 15: 4818-28 (2007).

Moreover, in the present description, the above described "extract" may be referred to as a "composition" in some cases.

An extract comprising a Stelliferin compound, or an extract or a composition comprising a Stelliferin compound and inhibiting the niche formation of cancer cells, can be obtained by fractionating a fraction, which has been separated and purified from Porifera by applying a separation and purification method such as a liquid-liquid extraction method, and then screening it, using, as an indicator, the presence or absence of the inhibitory activity of the fraction against cobblestone area formation, in a screening system for the cobblestone area formation inhibitory activity of a cultured cell system.

As the above described separation and purification method, a two-phase partition method, which is selected from the group consisting of, for example, a liquid-liquid extraction method, chromatography such as high performance liquid chromatography (HPLC), open column chromatography and affinity chromatography, and molecular sieve such as a Sephadex column, can be used.

As described in Examples below, a fraction having stronger activity, or an isolated and purified active compound can be obtained from the fat-soluble fraction of an alcohol extract from Porifera by further applying a combination of separation and purification methods. In the present invention, three types of Stelliferin compounds including a novel compound have been isolated from three fractions in these fractions obtained by fractionating Porifera, and the structures thereof have been identified and specified. The compounds include Stelliferin A, Stelliferin B, and Stelliferin compound 3 (code number: S09226.15-4) which is a novel Stelliferin compound.

Meanwhile, other than these three types of Stelliferin compounds obtained from Porifera, fat-soluble fractions from Porifera, such as fractions 15-2 (code number: S09226.15-2), 15-3 (code number: S09226.15-3), 15-6 (code number: S09226.15-6), 15-8 (code number: S09226.15-8), 15-9 (code number: S09226.15-9) and 15-10 (code number: S09226.15-10), are included in the extract of the present invention. In addition, compounds comprised in these fractions are included as unknown Stelliferin compounds having suppressive action against the niche formation of tumor cells in the compound of the present invention.

More specifically, the extract of the present invention is an extract extracted from Porifera (*Stelleta globostellata*) using a fat-soluble solvent, and the present extract comprises at least 2% (w/w) by dry weight of a Stelliferin compound, based on the total dry weight of the extract. A composition having suppressive action against the niche formation of tumor cells can be obtained from the extract. In the present description, the extract of the present invention may comprise such a Stelliferin compound in an amount of at least 3% (w/w), at least 5% (w/w), at least 10% (w/w), at least 15% (w/w), at least 20% (w/w), at least 25% (w/w), at least 30% (w/w), at least 35% (w/w), at least 40% (w/w), at least 45% (w/w), at least 50% (w/w), at least 55% (w/w), at least 60% (w/w), at least 65% (w/w), at least 70% (w/w), at least 75% (w/w), at least 80% (w/w), at least 85% (w/w), at least 90% (w/w), or at least 95% (w/w).

In the above described extract of the present invention, the above described fat-soluble fraction can be produced by performing the following steps:

(I) a step of extracting a fat-soluble fraction, using a water-insoluble organic solvent, from an extract, which has been extracted from Porifera using a water-soluble alcohol solvent, (II) a step of adding a high concentration of water-soluble alcohol solvent/aqueous solution and a water-insoluble aliphatic hydrocarbon solvent to the fat-soluble fraction obtained in the step (I) to perform liquid-liquid extraction, so as to recover a water-insoluble aliphatic hydrocarbon solvent layer (fraction 2-1), (III) a step of performing liquid-liquid extraction using an intermediate concentration of water-soluble alcohol solvent/ aqueous solution, which has been diluted by adding water to the high concentration of water-soluble alcohol solvent/aqueous solution layer obtained in the step (II) and a chlorinated hydrocarbon solvent, so as to recover a chlorinated hydrocarbon solvent fraction (fraction 2-2), and (IV) a step of subjecting the fraction 2-1 and the fraction 2-2 to concentration or solvent evaporation.

Moreover, in the above described extract of the present invention, the above described fat-soluble fraction can be produced by performing the following steps:

(I) a step of extracting a fat-soluble fraction, using a water-insoluble organic solvent, from an extract, which has been extracted from Porifera using a water-soluble alcohol solvent, (II) a step of adding a high concentration of water-soluble alcohol solvent/aqueous solution and a water-insoluble aliphatic hydrocarbon solvent to the fat-soluble fraction obtained in the step (I) to perform liquid-liquid extraction, so as to recover a water-insoluble aliphatic hydrocarbon solvent layer (fraction 2-1), (III) a step of performing liquid-liquid extraction using an intermediate concentration of water-soluble alcohol solvent/aqueous solution, which has been diluted by adding water to the high concentration of water-soluble alcohol solvent/aqueous solution layer obtained in the step (II) and a chlorinated hydrocarbon solvent, so as to recover a chlorinated hydrocarbon solvent fraction (fraction 2-2), and (IV) a step of subjecting the fraction 2-1 and the fraction 2-2 to concentration or solvent evaporation.

Furthermore, an extract comprising 76.3% or more of a Stelliferin compound can be obtained by further performing the following steps:

(V) a step of successively eluting the fraction 2-1 and the fraction 2-2 described in the above step (IV) according to silica gel column chromatography, using a non-polar solvent, a mixed solvent of a non-polar solvent and a polar solvent, and further, using a mixed solvent of a polar solvent and water in this order, so as to obtain a fraction having suppressive action against the niche formation of tumor cells, (VI) a step of purifying the fat-soluble fraction, before or after the above step (V), optionally, according to ODS reverse phase high performance liquid chromatography, by gradient chromatography using a mixed solvent of methanol and water, so as to obtain a fraction having suppressive action against the niche formation of tumor cells, and (VII) a step of further fractionating the fraction having suppressive action against the niche formation of tumor cells, which has been obtained in the above step (V) or (VI), according to high performance liquid chromatography, followed by isolation and purification, so as to obtain an extract comprising 76.3% or more of a Stelliferin compound.

The conditions for performing fractionation according to the above described high performance liquid chromatography to obtain the extract or compound of the present invention are, for example, the following conditions.

(i) ODS Reverse phase high performance liquid chromatography is performed under the following conditions:
Solid phase: COSMOSIL® 5C18 AR II
Solid phase size: 10 mm in inner diameter×250 mm in length
Mobile phase: 80% methanol aqueous solution
Flow rate: 2.0 mL/min, and a fraction is obtained at a retention time of 30 minutes or 34 minutes, and then, a step of subjecting the fraction obtained at a retention time of 30 minutes to solvent evaporation is performed to obtain an extract comprising 76.9% or more of a Stelliferin compound, or a step of subjecting the fraction obtained at a retention time of 34 minutes to solvent evaporation is performed to obtain an extract comprising 73.9% or more of a Stelliferin compound, otherwise, (ii) ODS reverse phase high performance liquid chromatography is performed under the following conditions:
Solid phase: COSMOSIL® 5C18 AR II
Solid phase size: 10 mm in inner diameter×250 mm in length
Mobile phase: 85% methanol aqueous solution
Flow rate: 2.0 mL/min, and the fraction obtained at a retention time of 40-42 minutes is subjected to solvent evaporation to obtain an extract comprising 76.9% of a Stelliferin compound.

With regard to the above described steps (I) to (VI), more specifically, the above described extract can be produced by performing the following steps, but the performed steps are not limited to:

(i) a step of performing liquid-liquid extraction on an extract extracted from Porifera using methanol, using water and a chlorinated hydrocarbon solvent comprising dichloromethane or chloroform, so as to recover a chlorinated hydrocarbon solvent fraction, (ii) a step of performing liquid-liquid extraction on a water-soluble fraction obtained in the step (i), using n-butanol, (iii) a step of mixing the chlorinated hydrocarbon solvent layer in the step (i) with an n-butanol layer in the step (ii), followed by concentration or solvent evaporation, and then adding a high concentration of methanol aqueous solution and n-hexane to the resultant, followed by liquid-liquid extraction, so as to recover an n-hexane layer, (iv) a step of performing liquid-liquid extraction using an intermediate concentration of methanol diluted by adding water to the high concentration of methanol layer in the step (iii) and a chlorinated hydrocarbon solvent, so as to recover a chlorinated hydrocarbon solvent fraction, and (v) a step of subjecting each fraction of the n-hexane of the step (iii) and the chlorinated hydrocarbon solvent layer of the step (iv) to concentration or solvent evaporation.

In the present description, the term "high concentration" is used to mean that the concentration is 75% or more, preferably 80% or more, and most preferably 90% or more.

In the present description, the term "intermediate concentration" is used to mean that the concentration is 30% or more and less than 75%, preferably 40% or more and less than 70%, and most preferably 60%.

Hereafter, methods of obtaining fractions 10-2 to 15-10 will be described as examples of extracts obtained by the method of the present invention, but the present method is not only limited to these methods.

The method for producing the extract of the present invention further comprises the following steps (vi) to (viii), in addition to the above described steps (i) to (v):

(vi) a step of successively eluting the fat-soluble fraction extracted with the water-insoluble solvent described in the step (v) according to silica gel column chromatography using a non-polar solvent, a mixed solvent of a non-polar solvent and a polar solvent, and further, using a mixed solvent of a polar solvent and water in this order, such that the non-polar solvent is converted to the polar solvent, so as to obtain a predetermined amount of fraction in the elution process, and then evaluating the suppressive action of the obtained fraction against the niche formation of tumor cells, thereby obtaining a fraction having the aforementioned activity, (vii) a step of further performing elution, before or after the step (vi), optionally, according to ODS reverse phase high performance liquid chromatography, by gradient chromatography using a mixed solvent of methanol and water, while successively increasing the content of methanol, to obtain a predetermined amount of fraction, thereby obtaining a fraction exhibiting suppressive action against the niche formation of tumor cells, so as to purify a fraction comprising an active compound, which is comprised in the above described fat-soluble fraction, and (viii) a step of further fractionating the fraction having suppressive action against the niche formation of tumor cells, which is obtained in the step (vi) or (vii), according to ODS reverse phase high performance liquid chromatography, and as a result, an extract comprising 76.3% or more of a novel Stelliferin compound (code number: S09226.15-4) can be obtained.

Examples of conditions applied to the isolation and purification method using the ODS reverse phase high performance liquid chromatography described in the step (viii) are the following.

(a) ODS Reverse phase high performance liquid chromatography is performed under the following conditions:
Solid phase: COSMOSIL® 5C18 AR II
Solid phase size: 10 mm in inner diameter×250 mm in length
Mobile phase: 80% methanol aqueous solution
Flow rate: 2.0 mL/min, and
a fraction is obtained at a retention time of 30 minutes or 34 minutes, and then,
a step of subjecting the fraction obtained at a retention time of 30 minutes to solvent evaporation is performed to obtain an extract comprising 76.9% or more of Stelliferin A, or
a step of subjecting the fraction obtained at a retention time of 34 minutes to solvent evaporation is performed to obtain an extract comprising 73.9% or more of Stelliferin B, otherwise, (b) ODS reverse phase high performance liquid chromatography is performed under the following conditions:
Solid phase: COSMOSIL® 5C18 AR II
Solid phase size: 10 mm in inner diameter×250 mm in length
Mobile phase: 85% methanol aqueous solution
Flow rate: 2.0 mL/min, and
a step of subjecting the fraction obtained at a retention time of 40-42 minutes to solvent evaporation is performed, so that an extract comprising 76.3% or more of a novel Stelliferin compound (code number: S09226.15-4) can be obtained.

Furthermore, according to the ODS reverse phase high performance liquid chromatography, under the same elution conditions as those described above, fractions having inhibitory action against the niche formation of tumor cells, which are indicated with code number: S09226.15-2 to code number: S09226.15-10, can be fractionated as fractions other than the above described Stelliferin compound (code number: S09226.15-4).

What is more, an example of the compound, which is included in the extract of the present invention and has an inhibitory action against the niche formation of tumor cells, can be a compound represented by the following formula (IX):

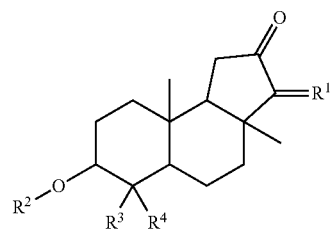

(IX)

wherein $R^1$ is selected from the group consisting of the following formula (X), formula (XI), and the above described terpene group:

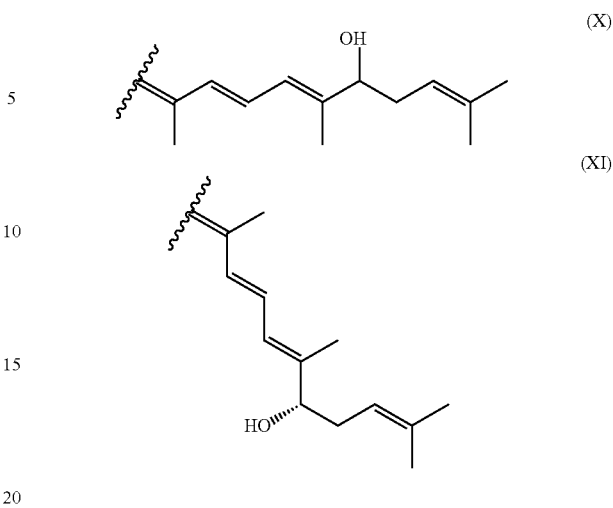

and $R^2$ is selected from the group consisting of H, —COCH$_3$, —COCH$_2$CH$_3$, —CO(CH$_2$)$_2$CH$_3$, —COCH(CH$_3$)$_2$, and —COC(CH$_3$)$_3$.

In the present description, the term "terpene" is also referred as "isoprenoid." In particular, when the terpene is derived from a natural product, it is called "terpenoid," and it means a compound having an isoprene unit, which is a compound containing 5 carbon atoms, or a derivative thereof. Thus, the terpene mainly means a compound derived from a natural product, but is not limited thereto.

The term "terpene group" means a substituent formed by removing one or two hydrogen atoms, and the like, from terpene or terpenoid, or a derivative thereof. Examples of the terpene include, but are not limited to, monoterpene, sesquiterpene, diterpene, sesterterpene, triterpene, tetraterpene (carotenoid), and polyterpene.

There is a case where the above described compound comprised in the fat-soluble fraction of the present invention is more specifically represented by the following formulae (XII) to (XIV).

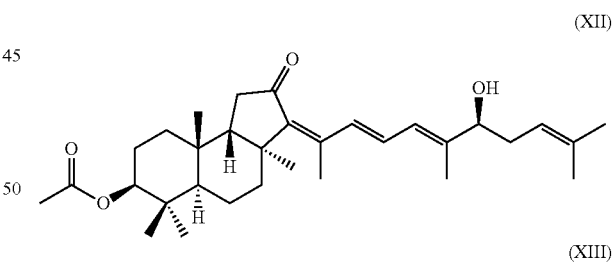

(XII)

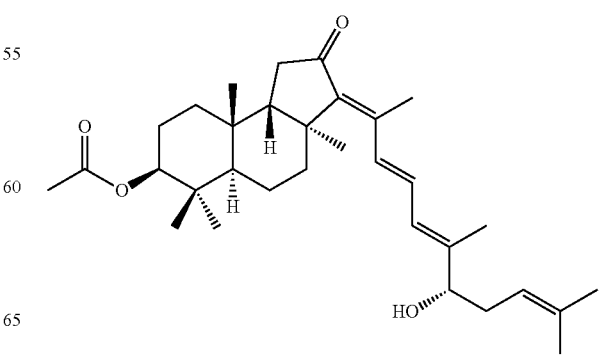

(XIII)

(XIV)

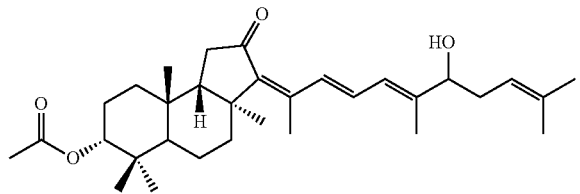

Furthermore, these Stelliferin A, B, or Stelliferin comprising S09226.15-4, or Stelliferin compounds comprising the fractions S09226.15-2 to S09226.15-10, which have been isolated from Porifera, are derivatized, so that the niche formation inhibitory activity can be further improved, or pharmacokinetics such as absorption, distribution, metabolism or excretion can be improved, thereby improving biological availability. Examples of the derivatization include: esterification performed on a hydroxyl group possessed by the Stelliferin structure according to a condensation reaction commonly used by a person skilled in the art; deacetylation on an acetyl ester possessed by a natural Stelliferin compound according to hydrolysis commonly used by a skilled person in the art; and re-esterification on a hydroxyl group of a deacetylated compound according to a condensation reaction commonly used by a person skilled in the art. Examples of the above described esterification or re-esterification include, but are not limited to, derivatization to acetylation, n-propyl esterification, isopropyl esterification, t-butyl esterification, etc.

In the present description, the term "prodrug" is used to mean a compound, which is metabolized in vivo, after it has been administered into a living body, and then generates the compound of the present invention as an active metabolite, or a salt thereof.

Examples of the Stelliferin derivative as a prodrug include compounds represented by the following formulae XV to XVII, or salts thereof.

(XV)

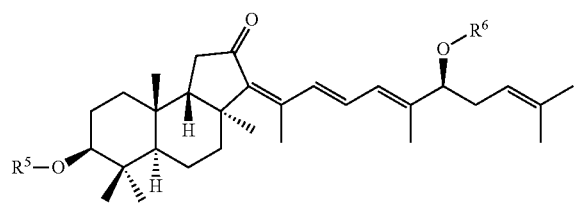

wherein $R^5$ and $R^6$ are each independently selected from the group consisting of H, an acetyl group, a n-propyl ester group, an isopropyl ester group, and a t-butyl ester group, but are not limited thereto.

(XVI)

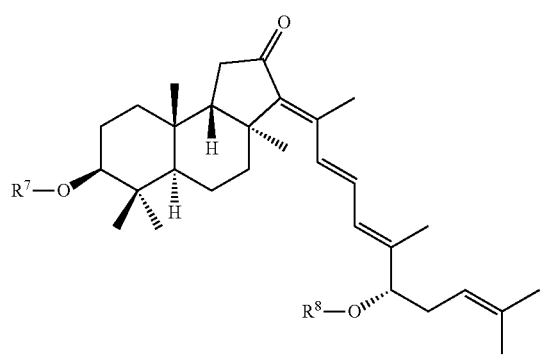

wherein $R^7$ and $R^9$ are each independently selected from the group consisting of H, an acetyl group, a n-propyl ester group, an isopropyl ester group, and a t-butyl ester group, but are not limited thereto.

(XVII)

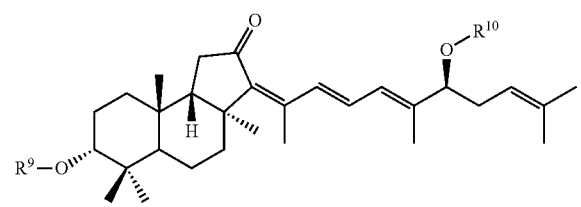

wherein $R^9$ and $R^{10}$ are each independently selected from the group consisting of H, an acetyl group, an n-propyl ester group, an isopropyl ester group, and a t-butyl ester group, but are not limited thereto.

In the present description, the term "fat-soluble solvent" means an insoluble, unpolar, non-polar, hydrophobic, lipophilic or fat-soluble solvent. Examples of the fat-soluble solvent include, but are not limited to, solvents such as dichloromethane, chloroform, n-hexane, n-butanol, ethyl acetate, benzene and toluene.

In the present description, the term "fat-soluble fraction" means a composition extracted from a mixture or admixture of multiple types of compounds, a natural product, and the like, using the above described fat-soluble solvent. For example, the fat-soluble fraction is a composition comprising a solute, which is obtained by distributing a disintegrated product of a natural product such as marine sponge into a fat-soluble solvent according to a separation method utilizing a liquid-liquid extraction method, then fractionating the fat-soluble solvent, and then distilling away or concentrating the solvent.

In the present description, the term "liquid-liquid extraction method" or "liquid-liquid distribution method" means an isolation and purification method, which utilizes a difference in the solubility of a substance of interest in two types of liquids well known to a person skilled in the art. However, the liquids used herein are not limited to the two types of liquids, as long as they can isolate and purify the substance of interest. For example, a two-phase partition method, such as liquid phase-solid phase, gaseous phase-solid phase, or gaseous phase-liquid phase, can be applied.

In the present description, the term "chlorinated hydrocarbon solvent" means a low molecular weight chlorinated hydrocarbon used as a solvent in the present technical field. Examples of the chlorinated hydrocarbon solvent include, but are not limited to, chloroform, dichloromethane (methylene chloride), trichloroethane, and tetrachloroethylene.

In the present description, the term "water-soluble organic solvent" means a polar organic solvent such as methyl alcohol (methanol) or ethyl alcohol (ethanol). There is a case where the term "polar solvent" is used herein to include the "water-soluble organic solvent" and "water."

In the present description, the term "water-soluble alcohol solvent" means a polar alcohol solvent such as methyl alcohol (methanol) or ethyl alcohol (ethanol). There is a case where the term "polar alcohol solvent" is used herein to include the "water-soluble alcohol solvent" and "water."

In the present description, the term "water-insoluble alcohol solvent" means an alcohol solvent showing water insolubility at an ordinary temperature. Examples of the water-insoluble alcohol solvent include, but are not limited to, n-butanol, 2-butanol, isobutyl alcohol, and isopentyl alcohol (isoamyl alcohol).

In the present description, the term "water-insoluble aliphatic hydrocarbon solvent" means a non-polar aliphatic hydrocarbon solvent, and it is, for example, n-hexane, but is not limited thereto.

In addition, when liquid-liquid extraction is carried out using a "chlorinated hydrocarbon solvent" or a "water-insoluble aliphatic hydrocarbon solvents," instead of the aforementioned solvents, or in addition to the aforementioned solvent, there can be used a water-insoluble solvent selected from the group consisting of: aromatic hydrocarbon solvents such as benzene, toluene, xylene and styrene; chlorinated aromatic hydrocarbon solvents such as chlorobenzene and ortho-dichlorobenzene; ester solvents such as methyl acetate, ethyl acetate, propyl acetate, isopropyl acetate, butyl acetate, isobutyl acetate, pentyl acetate (amyl acetate), and isopentyl acetate (isoamyl acetate); and ether solvents such as ethyl ether, 1,4-dioxane, and tetrahydrofuran.

In the present description, the term "water-insoluble solvent" means a solvent, which is separated into two layers when it is mixed with the same amount of water in a room temperature environment at about 23° C. The organic solvent, which does not show two-layer separation but is mixed with water, is referred to as a "water-soluble solvent."

In the present description, the term "alcohol extract" means an extract, which is extracted from a mixture or admixture of multiple types of compounds, a natural product, etc., using a water-soluble alcohol solvent such as methanol or ethanol, although the solvent is not limited thereto.

The term "niche" generally means an "ecological niche." In particular, the term "niche" is used in the present description to mean the "residence" of malignant tumor cells having the stem cell-like properties at the resting stage of cancer cells in a microenvironment in vivo. In chronic myelogenous leukemia, chronic myelogenous leukemic cells act as a cell population in the cobblestone area to form a niche. The niche tumor cells show resistance to antitumor agents, and it is considered that the regrowth of tumor cells due to activation of the niche tumor cells causes the recurrence of cancer after the remission thereof by treatments with antitumor agents (Patent Literature 1 to 3).

In the present description, the term "tumor" means cells or tissues, which have autonomously overgrown, and the tumor includes a "cancer" generating in epithelial cells (the mucosa in the digestive tube or the epidermal portion of cells such as hepatic cells), a "sarcoma" generating in non-epithelial cells (tissue cells which bind organs to each other, such as bone, cartilage or muscle), and "leukemia," "malignant lymphoma" and "multiple myeloma" generating in hematopoietic organs (blood, lymph, and bone marrow).

In the present description, the term "cancer stem cells (CSCs)" means cancer cells, which have the properties of stem cells. Such cancer stem cells have self-replication ability and pluripotency, and it is considered that cancer is developed from cancer stem cells as an origin. Cancer stem cells have already been found in various cancers. More specific examples of the cancer stem cells include maxillary cancer stem cells, pharyngeal cancer stem cells (including epipharynx, oropharynx and hypopharynx), laryngeal cancer stem cells, tongue cancer stem cells, thyroid cancer stem cells, breast cancer stem cells, lung cancer stem cells (non-small cell lung cancer stem cells and small cell lung cancer stem cells), esophageal cancer stem cells, stomach cancer stem cells, duodenal cancer stem cells, colorectal cancer stem cells (colon cancer stem cells and rectal cancer stem cells), liver cancer stem cells (hepatocellular carcinoma stem cells and bile duct cell carcinoma stem cells), gallbladder cancer stem cells, bile duct cancer stem cells, pancreatic cancer stem cells, anal cancer stem cells, kidney cancer stem cells, urinary tract cancer stem cells, bladder cancer stem cells, prostate cancer stem cells, penile cancer stem cells, testis (testicle) cancer stem cells, uterine cancer stem cells (cervical cancer stem cells and endometrial cancer stem cells), ovarian cancer stem cells, vulvar cancer stem cells, vaginal cancer stem cells, basal cell cancer stem cells, squamous cell cancer stem cells, leukemic stem cells, malignant lymphoma stem cells, and multiple myeloma stem cells.

In the present description, the term "leukemic stem cells (LSC)" means cells, which express a surface marker CD34 as a trait of hematopoietic stem cells, CD44 as a marker for cancer stem cells, which is a hyaluronic acid receptor associated with cell adhesiveness, and CD45 as one of the main structural components for lymphocyte membrane. Such leukemic stem cells form a niche at a resting stage of cell division in vivo, and have ability to proliferate leukemic cells when are activated, and thus, it is considered that these cells cause the recurrence of leukemia at a clinical remission stage of acute leukemia (Patent Literatures 1 to 3).

The term "cobblestone area (CA)" is also referred to as a "cobblestone-like structure formed area," and it means a cell population formed by the adhesion of cancer cells such as the above described leukemic stem cells as a group to supporting tissues constituted with mesenchymal cells, etc.

In the present description, the term "inhibitor against niche formation" means a compound having activity of inhibiting, suppressing, reducing or extinguishing the formation of the cobblestone area by cancer cells, or a salt thereof, or a composition comprising them. One example of the mechanism of inhibitory action against the niche formation is considered to be inhibition of adhesion of cancer cells forming a niche to supporting tissues. At present, antitumor agents used in the clinical sites, which have such inhibitory action against the niche formation, have not yet been reported.

In the present description, the term "antitumor agent" and the term "antitumor pharmaceutical composition" are used such that the two terms have the same meanings as each other. The "antitumor agent" or the "antitumor pharmaceutical composition" means a drug for ameliorating the symptoms of a patient having malignant tumor, or retarding progression of the symptoms, or improving the vital prognosis of the patient. The "antitumor agent" and the "antitumor pharmaceutical composition" include drugs classified into "antineoplastic agents" in the therapeutic category of Ministry of Health, Labour and Welfare in Japan, and candidate substances therefor. In the above described therapeutic category table, the antineoplastic agents" are classified into "alkylating agents", "antimetabolites", "antitumor antibiotics", "antitumor plant component formulations" and "other antineoplastic agents". Such antitumor agents have already been used in clinical sites. Specifically, examples of "molecular-targeted drugs" include ibritumomab tiuxetan, imatinib, erlotinib, gefitinib, gemtuzumab ozogamicin, sunitinib, cetuximab, sorafenib, dasatinib, tamibarotene, trastuzumab, tretinoin, panitumumab, bevacizumab, bortezomib, lapatinib, and rituximab; examples of "alkylating agents" include ifosfamide, cyclophosphamide, dacarbazine, temozolomide, nimustine, busulfan and melphalan; examples of "antimetabolites" include enocitabine, capecitabine, carmofur, gemcitabine, cytarabine, tegafur, tegafur-uracil, nelarabine, fluorouracil, fludarabine, pemetrexed, pentostatin and methotrexate; examples of "plant alkaloids" include irinotecan, etoposide, sobuzoxane, docetaxel, nogitekan, paclitaxel, vinorelbine, vincristine, vindesine and vinblastine; examples of "anticancer antibiotics" include actinomycin D, aclarubicin, idarubicin, epirubicin, daunorubicin, doxorubicin, pirarubicin, bleomycin, peplomycin, mitomycin C and mitoxantrone; examples of "platinum formulations" include oxaliplatin, carboplatin, cisplatin and nedaplatin; examples of "hormonal agents" include anastrozole, exemestane, ethinyl estradiol, chlormadinone, goserelin, tamoxifen, bicalutamide, flutamide, prednisolone, leuprorelin and letrozole; and examples of "biological response modifiers" include interferon α, interferon β, interferon γ, interleukin 2, ubenimex, dried BCG, and lentinan. The "antitumor agents" described in the present description are not limited to these agents, which have already been used in clinical sites.

Specifically, examples of the "malignant tumor", which is targeted by the "antitumor agent" or "antitumor pharmaceutical composition" of the present invention include, but are not limited to: "malignant tumors" in head and neck portions, such as "maxillary cancer", "pharyngeal cancer (including epipharynx, oropharynx and hypopharynx)", "laryngeal cancer", "tongue cancer", and "thyroid cancer"; malignant tumors in breast portions, such as "breast cancer" and "lung cancer (non-small cell lung cancer and small cell lung cancer)"; malignant tumors in digestive organs, such as "esophageal cancer", "stomach cancer", "duodenal cancer", "colorectal cancer (colon cancer and rectal cancer)", "liver cancer (hepatocellular carcinoma and bile duct cell carcinoma)", "gallbladder cancer", "bile duct cancer", "pancreatic cancer", and "anal cancer"; malignant tumors in urinary organs, such as "kidney cancer", "ureter cancer", "bladder cancer", "prostate cancer", "penile cancer", and "testis (testicle) cancer"; malignant tumors in genital organs, such as "uterine cancer (cervical cancer and endometrial cancer)", "ovarian cancer", "vulvar cancer", and "vaginal cancer"; malignant tumors of the skin, such as "basal cell carcinoma" and "squamous cell carcinoma"; and malignant tumors in hematopoietic organs (blood, lymph, and bone marrow), such as "leukemia", "malignant lymphoma", and "multiple myeloma".

The cell cycle of the above described leukemic stem cells (LSC) is stopped in the niche environment. Accordingly, LSC exhibits resistance to conventional antitumor agents, the effects of which depend on the cell cycle, and if such LSC is activated in the chronic stage of leukemia, the disease recurs. Thus, for prevention of the recurrence of leukemia, a strategy for provoking apoptosis to LSC as a target has been attempted (Patent Literature 1).

The extract of the present invention, which inhibits the niche formation of cancer cells, a compound isolated and purified from the extract, a derivative thereof, or a compound synthesized according to a total synthesis method with regard to the aforementioned compound or derivative, has an inhibitory action against the formation of a cobblestone area by human chronic myelogenous leukemic cells (CML), which have adhered to mesenchymal cells serving as supporting tissues, such as OP9 cells, and have the effect of increasing floating CML cells in a co-culture system in vitro. The CML, which has adhered to the supporting tissues, exhibits resistance to antitumor agents, but floating CML cells are provoked to undergo necrosis or apoptosis by antitumor agents. Therefore, cancer cells, which form a niche at the remission stage achieved by the treatment of a cancer patient with antitumor agents, such as leukemic stem cells, can be extinguished or reduced by using the niche formation inhibitory agent of the present invention in combination with antitumor agents, so that the recurrence of the cancer can be improved.

By adding pharmaceutically acceptable pharmaceutical additives to the above described extract or compound having inhibitory action against the niche formation of cancer cells, or a salt thereof, inhibitors against the niche formation of tumor cells, including oral agents and parenteral agents such as injections, can be produced.

Examples of the pharmaceutically acceptable salt include, but are not limited to, metal salts, ammonium salts, salts formed with organic bases, salts formed with inorganic acids, salts formed with organic acids, and salts formed with basic or acidic amino acids.

Preferred examples of the metal salts include: alkaline metal salts such as sodium salts and potassium salts; alkaline-earth metal salts such as calcium salts, magnesium salts, and barium salts; and aluminum salts.

Preferred examples of the salts formed with organic bases include salts formed with trimethylamine, triethylamine, pyridine, ethanolamine, diethanolamine, and triethanolamine.

Preferred examples of the salts formed with basic amino acids include salts formed with arginine, lysine, and ornithine. Preferred examples of the salts formed with acidic amino acids include salts formed with aspartic acid and glutamic acid.

At least one of the above described Stelliferin compound or a derivative thereof, or a pharmaceutically acceptable salt thereof or a solvate thereof is diluted, for example, with a solvent such as a normal saline, to a predetermined concentration and dose, and thereafter, pharmaceutically acceptable additives, such as a pH adjuster, are added to the resultant, so as to produce a pharmaceutical formulation. The thus produced pharmaceutical formulation can be administered to a patient.

The above described pharmaceutical formulation is a pharmaceutical composition comprising, as an active ingredient, the above described compound having niche formation inhibitory activity, or a salt or solvate thereof. In the present description, it is described as an inhibitor against niche formation, and it is preferably a pharmaceutical composition for preventing or treating malignant tumor, and by being combined with other antitumor agents, it can be used as a pharmaceutical composition for preventing the recurrence of malignant tumor.

Pharmaceutically acceptable additives for pharmaceutical products, which are used in preparation of the above described pharmaceutical formulation, can be prepared by adding additives known to a person skilled in the art, such as a stabilizer, an antioxidant, a pH adjuster, a buffer, a suspending agent, an emulsifier, or a surfactant. The type, usage, and dose of these additives for pharmaceutical products are described in the Japanese Pharmaceutical Excipients: Directory: 2007 (edited by IPEC Japan, Yakuji Nippo Sha, July 2007). The additives can be prepared in accordance with the description of this publication, and can be used.

More specifically, examples of the stabilizer that can be used herein include organic acids such as tartaric acid, citric acid, succinic acid, or fumaric acid; examples of the antioxidant that can be used herein include ascorbic acid, dibutylhydroxytoluene, or propyl gallate; examples of the pH adjuster that can be used herein include diluted hydrochloric acid or sodium hydroxide aqueous solution; examples of the buffer that can be used herein include citric acid, succinic acid, fumaric acid, tartaric acid or ascorbic acid, or salts thereof, glutamic acid, glutamine, glycine, aspartic acid, alanine or arginine, or salts thereof, magnesium oxide, zinc oxide, magnesium hydroxide, phosphoric acid or boric acid, or salts thereof; examples of the suspending agent or the emulsifier that can be used herein include lecithin, sucrose fatty acid ester, polyglycerin fatty acid ester, polyoxyethylene hydrogenated castor oil, polysorbate or a polyoxyethylene, polyoxypropylene copolymer; examples of the surfactant that can be used herein include polysorbate 80, sodium lauryl sulfate, or polyoxyethylene hydrogenated castor oil, but the examples of the additives are not limited thereto.

The amount of an active ingredient compound comprised in the above described formulation is not particularly limited, and it is selected, as appropriate, from a wide range. The amount of the active ingredient compound is generally 0.5% to 95% by weight, and preferably 1% to 30% by weight, based on the total weight of the composition.

The dose of the pharmaceutical composition according to the present invention is different depending on the degree of symptoms, age, sex, body weight, administration form/the type of salt, a difference in sensitivity to drugs, the specific type of disease, etc. In general, in the case of an adult, the present pharmaceutical composition is administered at a daily dose of about 1 mg to about 1000 mg (preferably about 10 mg to about 500 mg) by oral administration. In the case of an external agent, it is administered at a dose of about 1 mg to about 1000 mg (preferably about 10 mg to about 500 mg), and in the case of injection, it is administered at a dose of about 1 μg to about 3000 μg (preferably about 3 μg to about 3000 μg) per kg of body weight, once a day, or administered in 2 to 6 divided doses per a day.

The extract or compound of the present invention may be further used in combination with one to three other active ingredients having antitumor action. Such "other active ingredient(s)" are selected from the group consisting of ibritumomab tiuxetan, imatinib, erlotinib, gefitinib, gemtuzumab ozogamicin, sunitinib, cetuximab, sorafenib, dasatinib, tamibarotene, trastuzumab, tretinoin, panitumumab, bevacizumab, bortezomib, lapatinib, rituximab, ifosfamide, cyclophosphamide, dacarbazine, temozolomide, nimustine, busulfan, melphalan, enocitabine, capecitabine, carmofur, gemcitabine, cytarabine, tegafur, tegafur-uracil, nelarabine, fluorouracil, fludarabine, pemetrexed, pentostatin, methotrexate, irinotecan, etoposide, sobuzoxane, docetaxel, nogitekan, paclitaxel, vinorelbine, vincristine, vindesine, vinblastine, actinomycin D, aclarubicin, idarubicin, epirubicin, daunorubicin, doxorubicin, pirarubicin, bleomycin, peplomycin, mitomycin C, mitoxantrone, oxaliplatin, carboplatin, cisplatin, nedaplatin, anastrozole, exemestane, ethinylestradiol, rorumajinon, goserelin, tamoxifen, bicalutamide, flutamide, prednisolone, leuprorelin, letrozole, interferon α, interferon β, interferon γ, interleukin 2, ubenimex, dried BCG, and lentinan.

The above described "other active ingredient(s)" may be mixed with the extract or compound of the present invention or a salt thereof according to a known method, and they may be formulated in a single pharmaceutical composition (for example, a tablet, a powder agent, a granule, a capsule, a liquid agent, an injection, a suppository, a sustained release agent, etc.) and may be used in combination. Otherwise, the "other active ingredient(s)" and the extract or compound of the present invention or a salt thereof may be formulated, separately, and individual formulations may be then administered to a single patient simultaneously or at different times.

When the above described extract or compound of the present invention is used in combination with other active ingredient(s), the amounts of individual components are appropriately increased or decreased, depending on patient's symptoms, age, sex, body weight, medical history, etc., and then, individual components can be combined with one another and can be used.

Moreover, the above described extract and/or compound of the present invention can be used in a method for separating and/or sorting leukemic stem cells from tissues or a cell culture system comprising the leukemic stem cells and other cells.

The method for separating and/or sorting leukemic stem cells from tissues or a cell culture system comprising the leukemic stem cells of the present invention and other cells can be carried out by comprising a step of adding a culture solution containing the above described extract and/or the above described compound to tissues or a cell culture system comprising leukemic stem cells and other cells, then incubating the mixture, and then collecting floating cells.

Whether or not the collected floating cells are leukemic stem cells can be confirmed by examining a combination of cell markers specific to leukemic stem cells, and other properties specific to leukemic stem cells.

All literatures cited in the specification are incorporated herein in their entirety by reference. Embodiments of the present invention are described by way of Examples, which should not be construed as limiting the scope of the present invention.

Example 1

1. Materials and Experimental Methods
(1) Materials

In extraction and purification of an extract containing a Stelliferin compound, Porifera (scientific name: *Stelleta globostellata*, collection area: Kakeromajima (for S12111 fraction) and Mageshima (for S09226 fraction)) were used. OP9 cells and TF-1 cells used in experiments were obtained from ATCC; whereas, MB-1 cells were obtained from the Central Institute for Experimental Animals (Kawasaki city, Kanagawa prefecture).

Methanol, dichloromethane, chloroform, acetone, n-hexane, n-butanol and dimethylsulfoxide (DMSO) used for extracting a Stelliferin compound from an extract as mentioned above, in column chromatography for isolating/purifying the Stelliferin compound, and as an eluent for HPLC, were commercially available products of special grade or more. In the following description, the expressions of, e.g., "60% methanol", "85% methanol" and "90% methanol" mean methanol contents of 60%, 85% and 90% in a methanol-water mixture, respectively. Similarly, the expression of "85% acetonitrile" means an acetonitrile content of 85% in an aqueous solution.

(2) Method for Preparing Fat-Soluble Fraction and Water-Soluble Fraction as Samples for Screening A marine organism sample was extracted twice with 100% methanol. The extract was concentrated and then subjected to two-phase partition with chloroform and water to fractionate the extract into a fat-soluble fraction (S12111-E) and a water-soluble fraction (S12111-A). After the solvent was evaporated from the obtained fat-soluble fraction, the fat-soluble fraction was dissolved in DMSO (Wako Pure Chemical Industries, Ltd., Osaka) to prepare a solution having a concentration of 1 mg/mL; whereas, the water-soluble fraction was dissolved in 80% DMSO to prepare a solution having a concentration of 5 μg/mL.

(3) Screening Method

In individual wells of a 96-well plate, OP9 cells ($9.0 \times 10^3$) treated with 3 μg/mL mitomycin C (Sigma-Aldrich Co. LLC., USA) for 3 hours (37° C., 5% $CO_2$) were seeded and incubated at 37° C. under 5% $CO_2$. The culture liquid used herein was α MEM (Gibco) containing 20% inactivated FBS (MP Biomedicals, LLC., USA) and 1% penicillin-streptomycin (P/S, Gibco, Thermo Fisher Scientific Inc., USA). The following day, to the individual wells having OP9 cells seeded therein, MB-1 cells ($2.5 \times 10^3$) were seeded. In the co-culture of the OP9 cells and MB-1 cells, the culture liquid used herein was α MEM containing 10% inactivated FBS (Biowest SAS, France), 1% P/S, 1% non-essential amino acids (NEAA, Invitrogen, Thermo Fisher Scientific Inc.) and 10 μM β-mercaptoethanol (Gibco). Forty-eight hours later, a Porifera sample (2 μL) dissolved in DMSO was added and diluted five times to prepare four solutions different in concentration (10 μg/mL, 2 μg/mL, 0.4 μg/mL and 0.08 μg/mL). After incubation was performed for 48 hours at 37° C. under 5% $CO_2$, fixation was performed with 4% paraformaldehyde (Wako Pure Chemical Industries, Ltd.), nuclear-staining was performed with Hoechst 33342 (Dojindo Laboratories, Kumamoto) and observation was made with a microscope (Type IX71, Olympus Corporation Ltd., Tokyo). At this time, in order to obtain an LSC-specific effect in vitro and exclude a risk of side effect, two evaluation criteria: (1) having a CA formation inhibitory activity, and (2) having no strong toxicity to OP9 cells, were employed and determination was made by microscopic observation.

A method for evaluating a niche formation inhibitory action of individual subjects is outlined in FIG. 2A and FIG. 2B. and described specifically in the following sections.

(4) Method for Determining the Structure of Isolated Compound

In determining the structure of an isolated compound, measurement was performed by various types of NMR spectra: AVANCE400 (Bruker, Germany) and AVANCE600 (Bruker); and MS spectrum: HRESIMS Exactive plus (Thermo Fisher Scientific). In NMR measurement, a sample was dissolved in heavy chloroform and subjected to measurement. MS measurement was made in a positive mode (ionization method: electron spray ionization method, needle voltage: 3.84 kV, capillary temperature: 320° C.) using a solution of an isolated compound prepared to have a concentration of 5 µg/mL with 100% methanol.

(5) Measurement of Purity of Stelliferin Compound in Isolated/Purified Extract Fraction The purity of a Stelliferin compound contained in marine sponge was calculated by obtaining the ratio of a specific peak to a Stelliferin compound to the integral value of all peaks of the measurement sample, by use of TOF-MS.

The purities of fractions of Stelliferin A, Stelliferin B and Stelliferin compound S09226.15-4 isolated/purified were calculated based on the integral values of peaks of these compounds in $^1$H-NMR spectrum.

2. Experiment Results (1) Acquisition of Fat-Soluble Fraction from Porifera

Marine sponge *Stelleta globostellata* (192 g wet wt.) obtained in Kakeromajima was crushed and extracted with methanol (800 mL×3 times). The extract was concentrated and subjected to two-phase partition with dichloromethane and water. The water layer was further subjected to two-phase partition with normal butanol (n-butanol). The n-butanol layer was combined with the dichloromethane layer. The water layer obtained was designated as fraction 1-2. The combined organic layer was concentrated, and then, subjected to fractionation with solvents and separated into a fraction soluble in normal hexane (n-hexane), a fraction soluble in dichloromethane and a fraction soluble in 60% methanol, which were designated as fraction 2-1, fraction 2-2 and fraction 2-3, respectively (FIG. 3).

Marine sponge belonging to the same species (998 g wet wt.) and obtained in Mageshima was extracted with methanol (1000 mL×3 times). The extract was concentrated and subjected to two-phase partition with chloroform and water. The water layer was further subjected to two-phase partition with n-butanol. The n-butanol layer obtained was combined with the chloroform layer. The water layer obtained was designated as fraction 1-2. The combined organic layer was concentrated, and then, subjected to fractionation with solvents and separated into a fraction soluble in n-hexane, a fraction soluble in chloroform and a fraction soluble in 60% methanol, from which solvents were removed, and which were designated as fraction 2-1, fraction 2-2 and fraction 2-3, respectively (FIG. 3).

(2) Niche Formation Inhibitory Activity of Fat-Soluble Fraction (S12111 Fraction)

Fractions 1-2, 2-1, 2-2, 2-3 obtained from S12111 fraction were subjected to an activity evaluation test, which was performed in the same manner as described in the above section of "screening". The results are shown in Table 1 and FIG. 4.

TABLE 1

|  | S12111 fraction | | | |
| --- | --- | --- | --- | --- |
|  | 1-2 | 2-1 | 2-2 | 2-3 |
| CA formation inhibitory activity (µg/mL) | >10 | <0.08 | 2.0 | >10 |

A strong CA formation inhibitory activity was confirmed in fat-soluble fractions 2-1 and 2-2 obtained from S12111 fraction; whereas, substantially no activity was confirmed in fractions 1-2 and 2-3.

Of these fat-soluble fractions, fraction 2-2 derived from S09226 fraction was obtained in high yield and had a niche formation suppressive action described below. The content of a Stelliferin compound in this fraction was obtained by use of TOF-MS based on the ratio of a peak derived from the Stelliferin compound to the integral value of all peaks of the sample. The content was about 2.20; (w/w) per dry weight.

(3) Niche Formation Inhibitory Activity of Fat-Soluble Fraction (S09226 Fraction)

Fractions 1-2, 2-1, 2-2 and 2-3 were subjected to an activity evaluation test, which was performed in the same manner as described in the above section of "screening". The results are shown in Table 2.

TABLE 2

|  | S09226 fraction | | | |
| --- | --- | --- | --- | --- |
|  | 1-2 | 2-1 | 2-2 | 2-3 |
| CA formation inhibitory activity (µg/mL) | 10 | 2.0 | 0.89 | 10 |

A strong CA formation inhibitory activity was confirmed in fat-soluble fractions 2-1 and 2-2 derived from S09226 fraction; whereas only weak activity, similarly to the case of S12111 fraction, was confirmed in fractions 1-2 and 2-3.

(4) Purification and Isolation of Fractions Containing the Active Component in Fat-Soluble Fraction (S12111 Fraction)

Fraction 2-1 (n-hexane layer) was further fractionated by open silica gel column chromatography (inner diameter 2 cm×length 15 cm). Six types of solvents (150 mL for each), i.e., n-hexane, solvent mixtures of n-hexane:ethyl acetate=9:1, 8:2, 7:3 and 6:4, and a solvent mixture of chloroform: methanol:water=7:3:0.5, were separately and sequentially allowed to flow through the column. Each solvent was recovered in units of 25 mL and 32 fractions in total were obtained. Of them, 20 to 22 fractions were combined and the solvent was evaporated therefrom. The resultant fraction was designated as fraction 8-6 (FIG. 5).

Subsequently, fraction 8-6 (17.4 mg) was further purified by reversed phase HPLC. The column used herein was COSMOSIL® 5C18 ARII (inner diameter 10 mm×length 25 cm). Methanol (85%) was allowed to flow at a flow rate of 2 mL/min for 10 minutes, and then, the concentration of methanol was gradually changed up to 100% over 30 minutes. Two peaks which emerged at a retention time of 38 to 42 minutes were recovered and the solvent was evaporated. The obtained fraction was designated as fraction 9-4 (FIG. 5). An extract (2.1 mg) of a Stelliferin compound (identified later as Stelliferin A, fraction 10-3) was obtained at a retention time of 30 minutes and an extract (1.8 mg) of another type of Stelliferin compound (identified later as Stelliferin B, fraction 10-5) was obtained at a retention time of 34 minutes.

Fraction 9-4 (6.3 mg) was further purified by reversed phase HPLC. The conditions were the same as above except that 80% methanol was employed as the mobile phase. A Stelliferin compound (fraction 10-3) (2.1 mg) later identified as Stelliferin A was obtained at a retention time of 30 minutes and a Stelliferin compound (fraction 10-5) (1.8 mg) later identified as Stelliferin B, at a retention time of 34 minutes (FIG. 5).

(5) Niche Formation Inhibitory Activity of Fraction Purified and Isolated from Fat-Soluble Fraction Fractions 10-1 to 6 obtained from S12111 fraction by purification were subjected to an activity evaluation test. The results are shown in Table 3.

TABLE 3

|  | S12111 fraction | | | | | |
| --- | --- | --- | --- | --- | --- | --- |
|  | 10-1 | 10-2 | 10-3 | 10-4 | 10-5 | 10-6 |
| CA formation inhibitory activity (μg/mL) | >10 | >0.18 | 0.08 | 0.18 | 0.08 | 0.08 |

A strong CA formation inhibitory activity was confirmed in fractions 10-3 to 6 purified from S12111 fraction.

(6) Purification and Isolation of Fraction Containing Active Component in Fat-Soluble Fraction (S09226 Fraction)

Fraction 2-2 (chloroform layer) obtained from S09226 fraction was further fractionated by ODS flash column chromatography. Six types of solvents (500 mL for each), i.e., 50, 70% methanol, 70, 85% acetonitrile, 100% methanol, and a solvent mixture of chloroform:methanol:water=6:4:1, were separately and subsequently allowed to flow through the column to obtain fractions soluble in individual solvents, and then, the solvents were evaporated therefrom. Of the fractions, a fraction soluble in 100% methanol was designated as fraction 8-5 (FIG. 6).

Subsequently, fraction 8-5 (1293.6 mg) was further fractionated by open silica gel column chromatography. Six types of solvents (200 mL for each), i.e., chloroform, solvent mixtures of chloroform:methanol=19:1, 9:1, and solvent mixtures of chloroform:methanol:water=8:2:0.1, 7:3:0.5, 6:4:1, were separately and subsequently allowed to flow through the column. Each solvent was recovered in units of about 25 mL and 48 fractions in total were obtained. Of them, 4 to 8 fractions were combined and the solvent was evaporated therefrom. The resultant fraction was designated as fraction 9-2 (FIG. 6).

Fraction 9-2 (278.0 mg) was further purified by reversed phase HPLC. The conditions were the same as in the isolation process of Stelliferin A and B (fractions 10-3 and 10-5) except that 85% methanol was used as the mobile phase. The peak which emerged at a retention time of 40 to 42 minutes was recovered and the solvent was evaporated. Fractions 15-2 to 15-10 were obtained (FIG. 7A and FIG. 7B). Compound 3 (code number; S09226.15-4) was contained in fraction 15-4. Compound 4 (code number; S09226.15-5) was contained in fraction 15-5. Compound 5 (code number; S09226.15-7) was contained in fraction 15-7.

The content of Stelliferin A in fraction 10-3, the content of Stelliferin B in fraction 10-5, and the content of a novel compound S09226.15-4 in fraction 15-4 were obtained by $^1$H-NMR. In respective fractions (per dry weight), the content of Stelliferin A was about 76.9% (w/w) or more; the content of Stelliferin B was about 73.90 (w/w) or more; and the content of new Stelliferin compound S09226.15-4 was about 76.3% (w/w) or more.

Fractions 15-1 to 10 obtained from S09226 fraction were subjected to an activity evaluation test. The results are shown in Table 4.

TABLE 4

| CA formation inhibitory activity of S09226.15-1 to 8 | | | | | | | | | | |
| --- | --- | --- | --- | --- | --- | --- | --- | --- | --- | --- |
|  | S09226 fraction | | | | | | | | | |
|  | 15-1 | 15-2 | 15-3 | 15-4 | 15-5 | 15-6 | 15-7 | 15-8 | 15-9 | 15-10 |
| CA formation inhibitory activity (μg/mL) | >10 | 0.89 | 0.40 | 0.89 | 0.08 | 0.89 | 0.89 | 0.40 | 0.89 | 0.89 |

A strong CA formation inhibitory activity was confirmed in fractions 15-2 to 15-10 derived from S09226 fraction.

(7) Determination of Structure of Active Component Isolated from Fat-Soluble Fraction Fraction 10-3 and fraction 10-5 purified from S12111 fraction were subjected to $^1$H-$^{13}$C NMR and high-resolution MS measurement. In the high-resolution MS spectrum, fraction 10-3 was analyzed as $C_{32}H_{48}O_4$ (theoretical value; m/z 496.3553 (in the case where Na is added: 519.3445), actual measurement value; m/z 519.3445 [M Na]$^+$); and fraction 10-5 as $C_{32}H_{48}O_4$ (theoretical value; m/z 496.3553 (in the case where Na is added: 519.3445), actual measurement value m/z; 519.3446 [M+Na]$^+$). By these NMR spectral analyses, Stelliferin A and Stelliferin B were individually identified (FIG. 8 and FIG. 9).

Fraction 15-4, which was obtained by isolating/purifying S09226 fraction and which showed different HPLC retention time from those of Stelliferin A and Stelliferin B and exhibited a strong CA formation inhibitory activity, was also subjected to NMR and high-resolution MS measurement. In the high-resolution MS spectrum, a peak of $C_{32}H_{48}O_4Na$ (theoretical value; m/z 519.3445, actual measurement value; m/z 519.3443) was observed. Further, in the NMR spectrum, the compound contained in fraction 15-4 was identified as a novel Stelliferin compound (FIG. 10A and FIG. 10B).

Compound 4 and compound 5, which were respectively obtained from fraction 15-5 and fraction 15-7 exhibiting a strong CA formation inhibitory activity, were also subjected to $^1$H-NMR spectrum measurement. As a result, the main component of fraction 15-5 was identified as Stelliferin A; whereas the main component of fraction 15-7 was identified as Stelliferin B.

Example 2

(8) Evaluation of apoptosis inducing action on malignant tumor cells by combination use of Stelliferin compound having a niche formation inhibitory activity and antitumor agent A Stelliferin compound obtained by co-culturing of OP9 cells (which serve as support cells in CA formation in the mouse mesenchymal cells) and MB-1 cells was examined for the effect on CA formation.

To a 12-well plate, OP9 cells treated with MMC were seeded at a density of $1.6 \times 10^5$ cells per well. After culture was performed for one day, MB-1 cells were seeded at a density of $8.0 \times 10^4$ cells per well. After culture was performed for two days, Stelliferin A was added in a concentration of 0.4 μg/mL. After culture was performed for one day, imatinib was added in a concentration of 0.2 μM or 1.0 μM. After culture was performed for one day, apoptosis was detected in the manner described below.

Apoptosis was detected by use of NucView 488 Caspase-3 Assay Kit for Live Cells (Biotium, USA) or a fluorescent reagent JC-1 (Cayman Chemical, USA) which detects mitochondrial membrane potential difference.

In evaluation by NucView 488, 0.05% trypsin-EDTA was added to individual wells. After incubation for 4 minutes, the culture liquid was added. Aliquots were separately taken and then centrifuged (1,200 rpm, 4 minutes) to collect cells. Each of the suspensions of the cells collected was controlled so as to obtain a density of $1.0 \times 10^6$ cells per mL. Aliquots (200 μL) were separately taken from the suspensions. To the cells thus taken, 5 μL of NucView 488 substrate stock solution of NucView 488 Caspase-3 Assay Kit for Live Cells was added and incubated in the darkness at normal temperature for 20 minutes. Culture liquid (300 μL) was added and subjected to analysis by a cell sorter (Type SH-800, SONY Corporation, Tokyo). The ratio of green fluorescent positive cells per each well was calculated.

Compared to the case in the absence of Stelliferin A, in the cases in the presence of Stelliferin A, in both cases in the presence of imatinib of 0.2 μM and 1.0 μM, a peak on a high fluorescence intensity side in NucView, which represents caspase 3 activity, increased depending on each of the concentrations of Stelliferin A and imatinib (FIG. 11A).

These results are summarized in Table 5 and FIG. 11E. From these results, it was found that the ratio of MB-1 cells, which induced apoptosis depending on each of the concentrations of Stelliferin A and imatinib, statistically significantly (Student t test, p<0.05) increased.

TABLE 5

Apoptosis induction of MB-1 cells (%)

| | | Stelliferin A: absent | Stelliferin A: present at 0.4 μg/mL | p |
|---|---|---|---|---|
| Imatinib | Absent | 11.13 | 16.03 | 0.24 |
| | 0.2 μM | 8.07 | 22.39 | 0.03 |
| | 1.0 μM | 12.14 | 44.63 | 0.02 |

(9) Evaluation of Apoptosis Inducing Action by Imatinib Alone

Apoptosis inducing action by imatinib alone in a culture system of MB-1 cells alone was evaluated.

From a co-culture system with OP9 cells, MB-1 cells were purified by a cell sorter and seeded to 12-well plates at a density of $2.0 \times 10^5$ cells per well, and then, imatinib was added in a concentration of 0.2 μM or 1.0 μM. After culture was performed for one day, apoptosis was detected in the manner described below.

Apoptosis was detected by use of NucView 488 Caspase-3 Assay Kit for Live Cells (Biotium, USA) in the same manner as in the apoptosis detection performed in the co-culture system of MB-1 cells and OP9 cells.

Compared to MB-1 cells co-cultured in the absence of Stelliferin A, the MB-1 cells cultured alone exhibited high sensitivity to imatinib (FIG. 11C). From these results, it was found that MB-1 cells acquire drug resistance in the co-culture with OP9 cells.

(10) Evaluation of Apoptosis Inducing Action on Malignant Tumor Cells by Combination Use of a Stelliferin Compound Having a Niche Formation Inhibitory Activity and an Antitumor Agent, by JC-1 Reagent The effect of the Stelliferin compound on CA formed by co-culture of OP9 cells (serving as support cells for the CA formation in the mouse mesenchymal cells) and MB-1 cells was examined by apoptosis detection reagent JC-1.

To a 24-well plate, OP9 cells treated with MMC were seeded at a density of $8.0 \times 10^4$ cells per well. After culture was performed for one day, MB-1 cells were seeded at a density of $4.0 \times 10^4$ cells per well. After culture was performed for two days, Stelliferin A was added in a concentration of 0.4 μg/mL. After culture was performed for one day, imatinib was added in a concentration of 1.0 μM. After culture was performed for one day, apoptosis was detected in the manner described below.

Apoptosis was detected by JC-1 Mitochondrial Membrane Potential Assay Kit. To each well, 50 μL of JC-1 Reagent of JC-1 Mitochondrial Membrane Potential Assay Kit was added and incubation was carried out for 20 minutes. Thereafter, 0.05% trypsin-EDTA was added to each well and incubation was carried out for 4 minutes. After a culture liquid was added, aliquots were separately taken and then centrifuged (1,200 rpm, 4 minutes) to collect cells. The collected cells were separately suspended in 300 μL of a culture liquid and analyzed by a cell sorter (Type SH-800, SONY Corporation, Tokyo). The ratios of red fluorescent negative cells in individual wells were calculated.

Results

Compared to the case in the absence of Stelliferin A, in the case in the presence of Stelliferin A, a peak on the low fluorescence intensity side in JC-1 reagent, which represents that mitochondrial membrane potential difference disappeared, increased by addition of imatinib. In other words, it was confirmed that apoptosis was induced in the co-presence of Stelliferin A and imatinib (FIG. 12A and FIG. 12B). When the dose of imatinib was changed in the presence of Stelliferin A, it was confirmed that apoptosis was also induced in the dose-dependent manner of imatinib (FIG. 12C). These results coincided with the results obtained by NucView 488.

(11) Evaluation of the Effect of the Stelliferin Compound on the Stereoscopic Positional Relationship Between Cells The effect of a Stelliferin compound on the stereoscopic positional relationship between OP9 cells (which serve as support cells in CA formation in the mouse mesenchymal cells) and MB-1 cells was examined by using OP9 cells and MB-1 cells to which fluorescent proteins were separately introduced.

To a 35-mm dish having a glass bottom, OP9 cells, which were treated with MMC and to which fluorescent protein mCherry was introduced, were seeded at a density of $4.0 \times 10^5$ cells. After culture was performed for one day, fluorescent protein GFP introduced MB-1 cells were seeded at a density of $2.0 \times 10^5$ cells. After culture was performed for two days, Stelliferin A was added in a concentration of 0.4 µg/mL. After culture was performed for two days, the stereoscopic positional relationship between the cells was photographed with a confocal microscope (Type IX81, Olympus Corporation), and examined.

Results

It was observed that MB-1 cells dive under OP9 cell layer in the absence of Stelliferin A; however, MB-1 cells were exposed to the upper side of the OP9 cell layer in the presence of Stelliferin A (FIG. 13).

Brief Summary

From the above results, a Stelliferin compound having a suppressive activity against CA formation, which is observed in a co-culture system of MB-1 cells, which are leukemic stem-cell-like cells, and OP9 cells, was identified from a fraction isolated and purified from Porifera. The Stelliferin compound, as described in the results, does not directly exhibit apoptosis inducing action on MB-1 cells at the concentrations employed in the experiments; the action of the Stelliferin compound mentioned in the results is thus a specific action exerted in the co-culture system with the support cells. Although MB-1 cells dive under OP9 cell layer in the absence of Stelliferin A, MB-1 cells are exposed to the upper side of the OP9 cell layer in the presence of Stelliferin A. In other words, the action described in the results demonstrates that a Stelliferin compound suppressively acts against niche formation of leukemic stem cells and that the Stelliferin compound is useful for preventing recurrence of a malignant tumor by leukemic stem cells.

(12) Evaluation of Niche Formation Suppressive Action of S12111 Fraction in a Co-Culture System of TF-1 Cells and OP9 Cells In order to verify that the action of Stelliferin A to suppress niche formation by MB-1 cells is not specific to MB-1 cells, the actions of a fat-soluble fraction of S12111 and Stelliferin A against niche formation by TF-1 cells were evaluated in a co-culture system of TF-1 cells (which have leukemic stem-cell-like characteristics similarly to MB-1 cells) and OP9 cells.

The experiment was carried out basically in the same manner as employed in the evaluation with MB-1 cells mentioned above except that TF-1 cells (strain derived from human bone marrow erythroleukemia cells) were used in place of MB-1 cells. In evaluation of Stelliferin A, more specifically, evaluation of niche formation suppressive action of Stelliferin A in the co-culture system of TF-1 cells and OP9 cells, OP9 cells ($8.0 \times 10^4$) treated with MMC were seeded in individual wells of a 24-well plate. After culture was performed for one day, TF-1 cells ($4.0 \times 10^4$) were seeded. The culture liquid used herein was IMDM (Gibco) containing 10% inactivated FBS (Biowest SAS, France) and 1% P/S. After culture was performed for one day, medium was exchanged. After culture was performed for further one day, Stelliferin A was added in a concentration of 0.4 µg/mL. After culture was performed for two days, the presence or absence of CA formation was observed by a microscope.

A fat-soluble fraction (S12111-E) of S12111 and Stelliferin A suppressed niche formation by TF-1 cells, similarly to Stelliferin A having an effect on MB-1 cells (FIG. 14A and FIG. 14B). It was demonstrated that the niche formation against leukemic stem-cell-like cells shown by a Stelliferin compound is not an action specific to MB-1 cells, but commonly seen in the leukemic stem-cell-like cells (in FIG. 14, left view: control, right view: S12111-E fraction).

Example 3

(13) Examination of Rolls of OP9 Cells and MB-1 Cells in the Niche Formation Inhibitory Action of Stelliferin Compound Exerted in the Co-Culture System of OP9 Cells and MB-1 Cells Since the niche formation inhibitory action of a Stelliferin compound was an action specific to the co-culture systems of OP9 cells and MB-1 cells, and OP cells and TF-1 cells, a Stelliferin compound was allowed to act on OP9 cells and MB-1 cells in the co-culture system, the OP9 cells and the MB-1 cells were separated, and then, a Stelliferin compound was allowed to act separately on the cells. The roles of each of these cells were examined.

1) Examination of CA Reformation when a Stelliferin Compound was Added in a Co-Culture System of OP9 Cells and MB-1 Cells, and Thereafter, the Culture Medium was Exchanged On Day 1, OP9 cells were seeded in a culture medium in the same manner as above and incubated. On Day 2, MB-1 cells were seeded and co-cultured with the OP9 cells. On day 4, Stelliferin A was added so as to be 0.4 µg/mL and incubated. On Day 6, the culture medium was exchanged for a fresh medium containing no Stelliferin A. On Day 8, whether CA was reformed or not was examined and evaluated (FIG. 15A).

As a result, even if a Stelliferin compound was removed after the Stelliferin compound was allowed to act in the co-culture system of OP9 cells and MB-1 cells, CA was not reformed (FIG. 15A). Accordingly, it was demonstrated by the results that the effect of Stelliferin A lasts in the co-culture system of OP9 cells and MB-1 cells.

2) Examination of CA Reformation when a Stelliferin Compound was Allowed to Act in the Co-Culture System of OP9 Cells and MB-1 Cells, and then, Free Cells were Collected and Co-Cultured with Fresh OP9 Cells On Day 1, OP9 cells were seeded in a culture medium in the same manner as above and incubated. On Day 2, MB-1 cells were seeded and co-cultured with the OP9 cells. On day 4, Stelliferin A was added so as to be 0.4 µg/mL and incubated. On Day 6, free MB-1 cells were collected, added to fresh OP9 cells having been incubated since Day 5, and co-cultured in the absence of Stelliferin A. On Day 8, whether CA was reformed or not was examined.

As a result, when fresh OP9 cells and MB-1 cells on which Stelliferin A was allowed to act were co-cultured, CA was reformed (FIG. 15B). The results demonstrate that a target of the Stelliferin compound is not MB-1 cells.

3) Examination of CA Formation when a Stelliferin Compound was Allowed to Act on a Culture System of OP9 Cells Alone, Followed by Co-Culturing with MB-1 Cells not Exposed to the Stelliferin Compound On Day 1, OP9 cells were seeded in a culture medium in the same manner as above and incubated. On Day 2, Stelliferin A was added so as to be 0.4 μg/ml, and incubated. On Day 4, fresh MB-1 cells not exposed to Stelliferin A were seeded and co-cultured. On Day 6, whether CA was formed or not was examined. Also, for comparison, CA formation was examined in a control system where OP9 cells and MB-1 cells were co-cultured in the absence of Stelliferin A in accordance with the above schedule.

As a result, in the case where OP9 cells exposed to Stelliferin A and MB-1 cells not exposed to Stelliferin A were co-cultured, compared to the case where OP cells not exposed to Stelliferin A and MB-1 cells not exposed to Stelliferin A were co-cultured, the number of CAs formed was low (FIG. 15C). The results demonstrate that a Stelliferin compound acts on OP9 cells rather than MB-1 cells to exert the CA formation inhibitory action.

From the above results, it was demonstrated that a Stelliferin compound exerts CA formation inhibitory action in the co-culture system of leukemic stem-cell-like MB-1 cells and OP9 cells having a function as support cells, and acts on OP9 cells (serving as support cells) rather than MB-1 cells.

The experiments described in the specification are relevant to leukemic stem cells; however, the extract, composition, compound, inhibitor against the niche formation of tumor cells, pharmaceutical composition, prophylactic agent against recurrence, and method for separating and/or sorting leukemic stem cells are not limitedly applied to leukemic stem cells but can be applied to any cancer stem cells.

Accordingly, the above results demonstrate that administration of a pharmaceutical composition containing a Stelliferin compound including Stelliferin A in combination with, e.g., an antineoplastic agent or an anti-cancer agent, which exerts cytotoxicity to cancer cells, to cancer patients in a remission period in an effective dose can suppress or inhibit niche formation of cancer stem cells including leukemic stem cells and suppress recurrence of cancer including leukemia.

The results of the invention demonstrate that a Stelliferin compound provides a new treatment strategy for dealing with a recurrence of malignant tumors, particularly leukemia, based on different action from conventional antitumor agents.

The invention claimed is:

1. A method for treating a niche formation of leukemia cells or carcinoma cells, the method comprising:
   administering an effective dose of a compound of formulae (III) to (V):

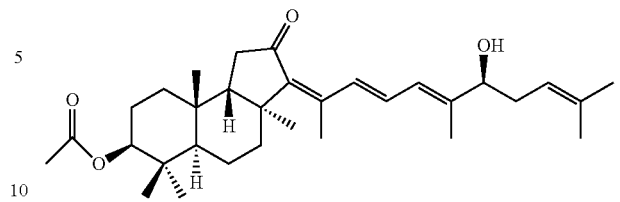

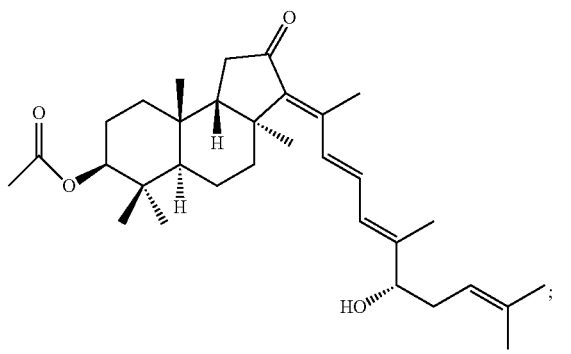

and

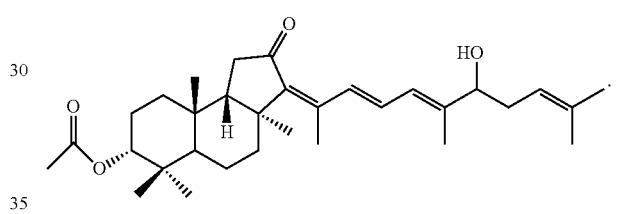

or a salt thereof to a patient in need thereof.

2. The method of claim 1, wherein the patient in need thereof has leukemia and the method treats niche formation of the leukemia cells.

3. The method of claim 1 which the patient in need thereof has a carcinoma and the method treats niche formation of the carcinoma cells.

4. The method of claim 1, wherein the patient in need thereof has lung carcinoma and the method treats niche formation of lung carcinoma cells.

5. The method of claim 1, wherein the patient in need thereof has breast cancer and the method treats niche formation of breast adenocarcinoma cells.

6. The method of claim 1, wherein the patient in need thereof has pancreatic adenocarcinoma and the method treats niche formation of pancreatic adenocarcinoma cells.

7. The method of claim 1, wherein the patient in need thereof has colorectal carcinoma and the method treats niche formation of colorectal carcinoma cells.

* * * * *